United States Patent
Rupasinghe et al.

(10) Patent No.: US 9,511,107 B2
(45) Date of Patent: *Dec. 6, 2016

(54) PHENOLIC COMPOSITIONS DERIVED FROM APPLE SKIN AND USES THEREOF

(71) Applicant: Dalhousie University, Halifax (CA)

(72) Inventors: Handunkutti Pathirannehalage Vasantha Rupasinghe, Truro (CA); George S. Robertson, Halifax (CA)

(73) Assignee: DALHOUSIE UNIVERSITY, Halifax (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/749,371

(22) Filed: Jun. 24, 2015

(65) Prior Publication Data
US 2015/0290274 A1    Oct. 15, 2015

Related U.S. Application Data

(63) Continuation of application No. 13/696,872, filed as application No. PCT/CA2011/050289 on May 10, 2011, now Pat. No. 9,101,649.

(60) Provisional application No. 61/333,091, filed on May 10, 2010.

(51) Int. Cl.
| | |
|---|---|
| *A61K 36/73* | (2006.01) |
| *A61K 31/19* | (2006.01) |
| *A61K 31/351* | (2006.01) |
| *A61K 31/352* | (2006.01) |
| *A61K 31/353* | (2006.01) |
| *A61K 31/7034* | (2006.01) |
| *A61K 31/7048* | (2006.01) |

(52) U.S. Cl.
CPC ............ *A61K 36/73* (2013.01); *A61K 31/19* (2013.01); *A61K 31/351* (2013.01); *A61K 31/352* (2013.01); *A61K 31/353* (2013.01); *A61K 31/7034* (2013.01); *A61K 31/7048* (2013.01)

(58) Field of Classification Search
None
See application file for complete search history.

(56) References Cited

U.S. PATENT DOCUMENTS

| | | | |
|---|---|---|---|
| 4,328,251 A | 5/1982 | Blanchaud et al. |
| 4,331,691 A | 5/1982 | Poovaiah et al. |
| 4,336,273 A | 6/1982 | Lee |
| 4,341,803 A | 7/1982 | Koshida et al. |
| 4,350,711 A | 9/1982 | Kahn et al. |
| 4,361,589 A | 11/1982 | Wauters et al. |
| 4,402,988 A | 9/1983 | Macfie, Jr. |
| 4,514,428 A | 4/1985 | Glass et al. |
| 4,520,574 A | 6/1985 | Sugisawa et al. |
| 4,542,033 A | 9/1985 | Agarwala |
| 4,551,348 A | 11/1985 | O'Mahony et al. |
| 4,626,434 A | 12/1986 | O'Mahony et al. |
| 4,735,813 A | 4/1988 | Spinoglio |
| 4,743,455 A | 5/1988 | Nichols |
| 4,818,549 A | 4/1989 | Steiner et al. |
| 4,879,122 A | 11/1989 | Seely, Jr. et al. |
| 4,889,730 A | 12/1989 | Roberts et al. |
| 4,948,609 A | 8/1990 | Nafisi-Movaghar |
| 5,172,487 A | 12/1992 | Hansen et al. |
| 5,188,861 A | 2/1993 | Mazin et al. |
| 5,523,106 A | 6/1996 | Gimmler et al. |
| 5,534,280 A | 7/1996 | Welch |
| 5,676,042 A | 10/1997 | Sakuma et al. |
| 5,690,725 A | 11/1997 | Tucker |
| 5,741,423 A | 4/1998 | Bates et al. |
| 5,840,354 A | 11/1998 | Baumann et al. |
| 5,939,117 A | 8/1999 | Chen et al. |
| 5,945,146 A | 8/1999 | Twinam |
| 6,440,410 B1 | 8/2002 | Yegorova |
| 6,440,449 B1 | 8/2002 | Hirschberg |
| 6,440,467 B2 | 8/2002 | Mann |
| 6,440,483 B1 | 8/2002 | Ghaedian et al. |
| 6,509,054 B1 | 1/2003 | Haddad et al. |
| 6,660,310 B2 | 12/2003 | Carlson |
| 6,733,797 B1 | 5/2004 | Summers |
| 6,740,344 B2 | 5/2004 | Murphy et al. |
| 6,780,449 B2 | 8/2004 | Razaa |
| 6,880,455 B1 | 4/2005 | Ghaedian et al. |
| 7,166,314 B2 | 1/2007 | Kuwa et al. |
| 7,186,701 B2 | 3/2007 | Kubota et al. |

(Continued)

FOREIGN PATENT DOCUMENTS

| | | |
|---|---|---|
| EP | 0 659 347 | 6/1995 |
| WO | 03/042133 A1 | 5/2003 |

(Continued)

OTHER PUBLICATIONS

Kamada et al., "Attenuation of lipid peroxidation and hyperlipidemia by quercetin glucoside in the aorta of high cholesterol-fed rabbit", Free Radical Research, Feb. 2005, vol. 39, No. 2, pp. 185-194.

(Continued)

*Primary Examiner* — Shaojia Anna Jiang
*Assistant Examiner* — Dale R Miller
(74) *Attorney, Agent, or Firm* — David A. Nauman; Borden Ladner Gervais LLP

(57) ABSTRACT

Described herein are phenolic compositions derived from apple skins. In particular, described herein are flavonoid-rich fractions derived from apple skin extract. The compositions are useful in the prevention and treatment of conditions associated with oxidative stress and/or inflammation, including certain neurodegenerative diseases. Methods of producing the compositions are also described.

34 Claims, 19 Drawing Sheets

(56) References Cited

U.S. PATENT DOCUMENTS

| | | |
|---|---|---|
| 7,198,811 B2 | 4/2007 | Paliyath et al. |
| 7,258,882 B2 | 8/2007 | Hankinson et al. |
| 7,264,835 B2 | 9/2007 | Funk |
| 7,399,491 B2 | 7/2008 | Palpu et al. |
| 7,413,757 B2 | 8/2008 | Klamerus |
| 7,507,423 B2 | 3/2009 | Wallace et al. |
| 7,993,693 B2 | 8/2011 | Bows et al. |
| 2003/0059515 A1 | 3/2003 | Haddad et al. |
| 2005/0147723 A1 | 7/2005 | Liu |
| 2006/0172012 A1 | 8/2006 | Finley et al. |
| 2007/0156011 A1 | 7/2007 | Westerkull |
| 2007/0191673 A1 | 8/2007 | Ball et al. |
| 2008/0026122 A1 | 1/2008 | Bows et al. |
| 2008/0044390 A1 | 2/2008 | Jin et al. |
| 2008/0131528 A1 | 6/2008 | Xu |
| 2008/0138480 A1 | 6/2008 | Bows et al. |
| 2008/0292607 A1 | 11/2008 | Mazzio et al. |
| 2013/0165396 A1 | 6/2013 | Rupasinghe et al. |

FOREIGN PATENT DOCUMENTS

| | | |
|---|---|---|
| WO | 2004/027074 A2 | 4/2004 |
| WO | 2004/052256 A1 | 6/2004 |
| WO | 2009/076776 A1 | 6/2009 |
| WO | 2011/140655 A1 | 11/2011 |

OTHER PUBLICATIONS

Katsanidis et al., "Evaluation of the antioxidant properties of barley flour and wild rice in uncooked and precooked ground beef patties", Journal of Food Science and Nutrition, 1997, vol. 10, No. 1, pp. 9-22.

Kaur et al., "Antioxidants in fruits and vegetables—the millennium's health", International Journal of Food Science and Technology, Oct. 2001, vol. 36, Issue 7, pp. 703-725.

Kim et al., "Phenolic Extraction from Apple Peel by Cellulases from Thermobifida fusca", Journal of Agricultural and Food Chemistry, Nov. 8, 2005, vol. 53, No. 24, pp. 9560-9565.

Kondo et al., "Antioxidative activity of apple skin or flesh extracts associated with fruit development on selected apple cultivars", Scientia Horticulturae, Dec. 2002, vol. 96, Issues 1-4, pp. 177-185.

Kremer et al., "n-3 Fatty acid supplements in rheumatoid arthritis", American Journal of Clinical Nutrition, 2000, vol. 71, pp. 349S-351S.

Lemanska et al., "The influence of pH on antioxidant properties and the mechanism of antioxidant action of hydroxyflavones", Free Radical Biology and Medicine, 2001, vol. 31, No. 7, pp. 869-881.

Leontowicz et al., "Apple and pear peel and pulp and their influence on plasma lipids and antioxidant potentials in rats fed cholesterol-containing diets", Journal of Agricultural and Food Chemistry, Aug. 2003, vol. 51, No. 19, pp. 5780-5785.

Leontowicz et al., "Apple peels and pulp as a source of bioactive compounds and their influence on digestibility and ipid profiles in normal and atherogenic rats", Medycyna Wet., 2007, vol. 63, No. 11, pp. 1434-1436.

Leontowicz et al., "Comparative content of some bioactive compounds in apples, peaches and pears and their influence on lipids and antioxidant capacity in rats", Journal of Nutritional Biochemistry, Oct. 2002, vol. 13, No. 10, pp. 603-610.

Leontowicz et al., "The nutritional and metabolic indices in rats fed cholesterol-containing diets supplemented with lurian at different stages of ripening", Biofactors, 2007, vol. 29, pp. 123-136.

Levine S., "Anoxic-ischemic encephalopathy in rats", American Journal of Pathology, Jan. 1960, vol. 36, No. 1, pp. 1-17.

Loke et al., "Quercetin and its in vivo metabolites inhibit neutrophil-mediated low-density lipoprotein oxidation", Journal of Agricultural Food and Chemistry, May 2008, vol. 56, No. 10, pp. 3609-3615.

Lotito et al., "Consumption of flavonoid-rich foods and increased plasma antioxidant capacity in humans: cause, aonsequence, or epiphenomenon?", Free Radical Biology & Medicine, Dec. 2006, vol. 41, No. 12, pp. 1727-1746.

Lotito et al., "Relevance of apple polyphenols as antioxidants in human plasma: contrasting in vitro and in vivo effects", Free Radical Biology & Medicine, Jan. 15, 2004; vol. 36, No. 2, pp. 201-211.

Lowry et al., "Protein measurement with the folin phenol reagent", The Journal of Biological Chemistry, May 28, 1951, vol. 193, pp. 265-275.

Lu et al., "Antioxidant and radical scavenging activities of polyphenols from apple pomace", Food Chemistry, Jan. 2000, vol. 68, Issue 1, pp. 81-85.

Luthria et al., "A systematic approach for extraction of phenolic compounds using parsley (Petroselinum crispum) flakes as a model substrate", Journal of the Science of Food and Agriculture, Jul. 2006, vol. 86, Issue 9, pp. 1350-1358.

McGhie et al., "Cultivar and Growing Region Determine the Antioxidant Polyphenolic Concentration and Composition of Apples Grown in New Zealand", Journal of Agricultural and Food Chemistry, Mar. 2005, vol. 53, 3065-3070.

Montero et al., "Oxidation stability of muscle with quercetin and rosemary during thermal and high-pressure gelation", Food Chemistry, 2005, vol. 93, No. 1. pp. 17-23.

Moore et al., "Increased X-linked inhibitor of apoptosis (XIAP) expression exacerbates experimental autoimmune P.ncephalomyelitis", Journal of Neuroimmunology, 2008, vol. 203, pp. 79-93.

Moore et al., "Inhibitor of apoptosis protein (IAP) profiling in experimental autoimmune encephalomyelitis (EAE) implicates increased XIAP in T lymphocytes", Journal of Neuroimmunology, 2008, vol. 193, No. 1-2, pp. 94-105.

Moore et al., "Peripheral phosphodiesterase 4 inhibition produced by 4-[2-(3,4-Bis-difluoromethoxyphenyl)-2-[4-(1,1,1,3,3,3-hexafluoro-2-hydroxypropan-2-yl)-phenyl]-ethyl]-3-methylpyridine-1-oxide (L-826,141) prevents experimental autoimmune encephalomyelitis", Journal of Pharmacology and Experimental Therapeutics, Oct. 2006, vol. 319, No. 1, pp. 63-72.

Naczk et al., "Extraction and analysis of phenolics in food", Journal of Chromatography A, Oct. 2004, vol. 1054, ssues 1-2, pp. 95-111.

Okuda et al., "Impact of lipid physical state on the oxidation of methyl linolenate in oil-in-water emulsions", Journal of Agricultural and Food Chemistry, Nov. 2005, vol. 53, No. 24, pp. 9624-9628.

Osawa et al., "Novel type of antioxidant isolated from leaf wax of Eucalyptus leaves", Agric Biol Chem, 1981, vol. 45, No. 3, pp. 735-739.

Ozsoy et al., "Antioxidant activity of Smilax excelsa L. leaf extracts", Food Chemistry, 2008, vol. 110, pp. 571-583.

Pazos et al., "Activity of grape polyphenols as inhibitors of the oxidation of fish lipids and frozen fish muscle", Food chemistry, 2005, vol. 92, pp. 547-557.

Peluso MR, "Flavonoids attenuate cardiovascular disease, inhibit phosphodiesterase, and modulate lipid lomeostasis in adipose tissue and liver", Experimental Biology and Medicine, Sep. 2006, vol. 231, No. 8, pp. 1287-1299.

Perez-Vizcaino et al., "Endothelial function and cardiovascular disease: effects of quercetin and wine polyphenols", Free Radical Research, Oct. 2006, vol. 40, No. 10, pp. 1054-1065.

Powell et al., "Cognitive impairments in the STOP null mouse model of schizophrenia", Behavioral Neuroscience, May 2009, vol. 121, No. 5, pp. 826-835.

Powell et al., "Neonatal Ventral Hippocampal Lesions Produce an Elevation of ΔFosB-like Protein(s) in the Rodent Neocortex", Neuropsychopharmacology, 2006, vol. 31, No. 4, pp. 700-711.

Prior et al, "Standardized methods for the determination of antioxidant capacity and phenolics in foods and dietary supplements", Journal of Agricultural and Food Chemistry, Apr. 2005, vol. 53, No. 10, pp. 4290-4302.

Robertson et al., "Schizophrenia: an integrative approach to modelling a complex disorder", Journal of Psychiatry Neurosci, 2006, vol. 31, No. 3, pp. 157-167.

(56) References Cited

OTHER PUBLICATIONS

Rosa et al., "Melatonin protects the liver and erythrocytes against oxidative stress in cirrhotic rats", Experimental gastroenterology, Jan.-Mar. 2010, vol. 47, No. 1, pp. 72-78.
Ruiz et al., "Dietary administration of high doses of pterostilbene and quercetin to mice is not toxic", Journal of Agricultural and Food Chemistry, Mar. 2009, vol. 57, No. 8, pp. 3180-3186.
Rupasinghe et al. "Supercritical Carbon Dioxide Extraction of Flavanoids from Apple Skin", the 23rd International conference on Polyphenols, Winnipeg, Manitoba, Aug. 25, 2006. Polyphenols communication 23; pp. 233-234.
Rupasinghe et al., "Antioxidant protection of eicosapentaenoic acid and fish oil oxidation by polyphenolic-enriched apple skin extract"; Journal of Agricultural and Food Chemistry, Jan. 27, 2010, vol. 58, No. 5, pp. 1233-1239.
Rupasinghe et al., "Effect of baking on dietary fibre and phenolics of muffins incorporated with apple skin powder", Food Chemistry, Apr. 1, 2008, vol. 107, Issue 3, pp. 1217-1224.
Rupasinghe V., "Using change for success: Fruit-based bio-product research at the Nova Scotia Agricultural college", Nova Scotia Fruit Growers' Association 2003 Annual Report, Kentville, NS, Canada, 2003, p. 66-69.
Sandmeier D., "Prooxidative effects of spices under the influence of light", Fett/Lipid, 1996, vol. 98, Issue 6, pp. 199-202.
Simopoulos et al., "The importance of the ratio of omega-6/omega-3 essential fatty acids", Biomedicine & Pharmacotherapy, 2002, vol. 56, pp. 365-379.
Singleton et al., "Analysis of total phenols and other oxidation substrates and antioxidants by means of Folin-Ciocalteu reagent", Methods Enzymol, 1999, pp. 152-178.
Soundararajan et al., "Quercetin 3-glucoside protects neuroblastoma (SH-SY5Y) cells in vitro against oxidative damage by inducing sterol regulatory element-binding protein-2-mediated cholesterol biosynthesis", Journal of Biological Chemistry, Jan. 25, 2008, vol. 283, No. 4, pp. 2231-2245.
Soundararajan et al., "Triptolide: an inhibitor of a disintegrin and metalloproteinase 10 (ADAM10) in cancer cells", Cancer Biology & Therapy, Nov. 1, 2009, vol. 8, No. 21, pp. 2054-2062.
Tabata et al., "Isolation and evaluation of the radical-scavenging activity of the antioxidants in the leaves of an edible plant, Mallotus Japonicus", Food Chemistry, 2008, vol. 109, pp. 64-71.
Thorne et al., "Lack of TIMP-1 increases severity of experimental autoimmune encephalomyelitis: Effects of larbepoetin alfa on TIMP-1 null and wild-type mice", Journal of Neuroimmunology, 2009, vol. 211, pp. 92-100.
Tsao et al., "Which polyphenolic compounds contribute to the total antioxidant activities of apple?", Journal of Agricultural and Food Chemistry, Jun. 15, 2005, vol. 53, No. 12, pp. 4989-4995.
Tsimidou et al., "Evaluation of oregano antioxidant activity in mackerel oil", Food Research International, 1995, vol. 28, No. 4, pp. 431-433.
Vidal et al., "The mouth-feel properties of grape and apple proanthocyanidins in a wine-like medium", Journal of the Science of Food and Agriculture, 2003, vol. 83, pp. 564-573.
Vinson et al., "Beneficial effects of a novel IH636 grape seed proanthocyanidin extract and a niacin-bound chromium in a hamster atherosclerosis model", Molecular and Cellular Biochemistry, Nov. 2002, vol. 240, No. 1-2, pp. 99-103.
Vinson et al., "Phenolic antioxidant quantity and quality in foods: fruits", Journal of Agricultural and Food Chemistry, Oct. 2001, vol. 49, pp. 5315-5321.
Wanasundara et al., "Antioxidant and pro-oxidant activity of green tea extracts in marine oils", Food Chemistry, 1998, vol. 63, No. 3, pp. 335-342.
Wang et al., "Constituents of the flowers of Punica granatum", Fitoterapia, Dec. 2006, vol. 77, Issues 7-8, pp. 534-537.
Wang et al., "Effects of policosanols and phytosterols on lipid levels and cholesterol biosynthesis in hamsters", Lipids, Feb. 2003, vol. 38, No. 2, pp. 165-170.
Wang et al., "Over-expression of X-linked inhibitor of apoptosis protein slows presbycusis in C57BL/6J mice", Neurobiology of Aging, 2010, vol. 31, pp. 1238-1249.
Wang et al., "Very long chain fatty acids (policosanols) and phytosterols affect plasma lipid levels and cholesterol biosynthesis in hamsters", Metabolism Clinical and Experimental, Apr. 2005, vol. 54, Issue 4, pp. 508-514.
Wang et al., "n-3 Fatty Acids from fish or fish-oil supplements, but not alphalinolenic acid, benefit cardiovascular disease outcomes in primary- and secondary-prevention studies: a systematic review", American Journal of Clinical Nutrition, 2006, vol. 84, pp. 5-17.
Weichselbaum et al., "Apple polyphenols and cardiovascular disease—a review of the evidence", British Nutrition Foundation, Jun. 2010, vol. 35, Issue 2, pp. 92-101.
Wettasinghe et al., Antioxidant and free radical-scavenging properties of ethanolic extracts of defatted borage (Borago officinalis L.) seeds: Food Chemistry, 1999, vol. 67, No. 4, pp. 399-414.
Wiesner et al., "Increased expression of the adipokine genes resistin and fasting-induced adipose factor in hypoxic/ischaemic mouse brain", Neuroreport, Jul. 31, 2006, vol. 17, No. 11, pp. 1195-1198.
Wigmore et al., "The Effect of Polyunsaturated fatty acids on the progress of cachexia in patients with pancreatic cancer", Nutrition, 1996, vol. 12, No. 1, pp. S27-S30.
Williams et al., "Flavonoids: Antioxidants or Signalling Molecules?", Free Radical Biology and Medicine, Apr. 1, 2004, vol. 36, Issue 7, pp. 838-849.
Wojdylo et al., "Polyphenolic Compounds and Antioxidant Activity of New and Old Apple Varieties", Journal of Agricultural and Food Chemistry, Jul. 2008, vol. 56, No. 15, pp. 6520-6530.
Wolfe et al., "Apple peels as a value-added food ingredient", Journal of Agricultural Food Chemistry, Mar. 12, 2003, vol. 51, No. 6, pp. 1676-1683.
Wolfe et al., "Antioxidant Activity of Apple Peels", Journal of Agricultural Food Chemistry, Jan. 2003, vol. 51, pp. 509-614.
Xu et al., "Comparative studies on the antioxidant activities of nine common food legumes against copper-induced human low-density lipoprotein oxidation in vitro", Journal of Food Science, Sep. 2007, vol. 72, No. 7, pp. S522-S527.
Yamamoto et al., "Inhibitory effect of quercetin metabolites and their related derivatives on copper ion-induced lipid peroxidation in human low-density lipoprotein", Archives of Biochemistry and Biophysics, Dec. 15, 1999, vol. 372, No. 2, pp. 347-354.
Yousaf et al., "Recovery of Polyphenolic Compounds from Apple Peels", Poster—Tree Fruit BioProduct Research Program, Nova Scotia Agricultural College, Truro, NS, Canada.
Zehntner et al., "X-linked Inhibitor of Apoptosis Regulates T Cell Effector Function" Journal of Immunology, 2007, vol. 179, No. 11, pp. 7553-7560.
Zhang et al., "Characterization of antioxidants present in hawthorn fruits", Journal of Nutritional Biochemistry, Mar. 2001, vol. 12, No. 3, pp. 144-152.
Zhang et al., "Choosing hamsters but not rats as a model for studying plasma cholesterol-lowering activity of functional foods", Molecular Nutrition and Food Research, Jul. 2009, vol. 53, No. 7, pp. 921-930.
Zhang et al., "Ursane triterpenoids inhibit atherosclerosis and xanthoma in LDL receptor knockout mice", Cardiovascular ardiovascular Drugs and Therapy, Oct. 2006, vol. 20, No. 5, pp. 349-357.
European Application No. 08862365.7, Extended European Search Report dated Mar. 18, 2011.
Alberto et al., "Antimicrobial effect of polyphenols from apple skins on human bacterial pathogens", Electronic Journal of Biotechnology, 2006, vol. 9, No. 3, pp. 205-209.
Sigma-Aldrich online products, Sigma-Aldrich Corporation, Saint Louis, Missouri USA, available at http://www.sigmaaldrich.com/chemistry/solvents/products.html?TablePage=17292456 last visited Jun. 13, 2014.
"Notification of Material Filed Under Section 27 in AU App No. 2011252720," mailed Jan. 6, 2014, AU App No. 2011252720, filed May 10, 2011, titled "Phenolic compositions derived from apple skin and uses thereof", 47 pages.

(56) References Cited

OTHER PUBLICATIONS

He, Xiangjiu et al., "Phytochemicals of Apple Peels: Isolation, Structure Elucidation and Their Antiproliferative and Antioxidant Activities", Journal of Agricultural and Chemistry, vol. 56. No. 21, Nov. 12, 2008, pp. 9905-9910.
Schirrmacher Georg et al. "Antioxidative potential of flavonoid-rich extracts as new quality marker for different apple varieties." Journal of Applied Botany, vol. 77, No. 5-6, Dec. 2003, pp. 163-166.
Liu, R. H. (2003). Health benefits of fruit and vegetables are from additive and synergistic combinations of phytochemicals. The American Journal of clinical nutrition, 78 (3), 517S-520S.
European Commission. (2003). Guideline Excipients in the label and package leaflet of medicinal products for human use. CPMP/463/00. EC: Brussels.
Curin Y., & Andriantsitohaina, R. (2005). Polyphenols as potential therapeutical agents against cardiovascular diseases. Pharmacological reports, 57, 97.
Ramassamy, C. (2006). Emerging role of polyphenolic compounds in the treatment of neurodegenerative diseases: a review of their intracellular targets. European journal of pharmacology, 545(1), 51-64.
"Prevention" in Glossary of medical education terms: Part 1-7. Wojtczak, A., Ed. Medical Teacher. vol. 24, Nos. 2-6 and vol. 25, No. 1&2. 2002.
Décordé, K., Teissédre, P. L., Auger, C., Cristol, J. P., & Rouanet, J. M. (2008), Phenolics from purple grape, apple, purple grape juice and apple juice prevent early atherosclerosis induced by an atherogenic diet in hamsters. Molecular nutrition & food research, 52(4), 400-407.
Khanizadeh, S., Tsao, R., Rekika, D., Yang, R., & DeEll, J. (2007), Phenolic composition and antioxidant activity of selected apple genotypes. Journal of Food Agriculture and Environment, 5(1), 61.
English translation of "Al-Qaanon-fil-Tibb, vol. II", by Abu Ali Ibn-e-Sina, Institute of History of Medicine and Medical Research, 1987 AD, p. No. 4-8.
English translation of "Bhavaprakasa—Edited & translated by Brahmashankara Misra & RupaLalaji Vaisya, Part-I", by Bhavamisra, Chaukhambha Sanskrit Sansthan, Edn. 9th, 1999, p. No. 9-13.
English translation of "Siddhabhesajamanimalah—Commentary by Kaladhara Bhatta", by Krsnarama Bhatta, Chaukhambha Krishnadas Academy, Edn. 3rd 2003, p. No. 14-18.
Alirezaei et al., "Elevated ATG5 expression in autoimmune demyelination and multiple sclerosis", Autophagy, Feb. 2009, vol. 5, No. 2, pp. 152-158.
Allouche et al. "Antioxidant and antiatherogenic activities of pentacyclic triterpenic diols and acids", Food and Chemical Toxicology, Oct. 2010, vol. 48, Iss. 10, pp. 2885-2890.
Alonso-Salces et al., "A validated solid—liquid extraction method for the HPLC determination of polyphenols in apple tissues: Comparison with pressurised liquid extraction", Talanta, Feb. 15, 2005, vol. 65, No. 3, pp. 654-662.
Amarowicz et al., "Antioxidant activity of various fractions of non-tannin phenolics of canola hulls", Journal of Agricultral and Food Chemistry, Jun. 16, 2000, vol. 48, No. 7, pp. 2755-2759.
Andrikopoulos et al., "Biological activity of some naturally occurring resins, gums and pigments against in vitro LDL oxidation", May 2003, vol. 17, Issue 5, pp. 501-507.
Andrikopoulos et al., "Inhibitory activity of minor polyphenolic and nonpolyphenolic constituents of olive oil against in vitro low-density lipoprotein oxidation", Journal of Medicinal Food, 2002, vol. 5, No. 1, pp. 1-7.
Aprikian et al., "Apple favourably affects parameters of cholesterol metabolism and of anti-oxidative protection in cholesterol-fed rats", Food Chemistry, Dec. 2001, vol. 75, Issue 4, pp. 445-452.
Aprikian et al., "Lyophilized Apple Counteracts the Development of Hypercholesterolemia, Oxidative Stress, and Renal Dysfunction in Obese Zucker Rats", The Journal of Nutrition, Jul. 1, 2002, vol. 132, No. 7, pp. 1969-1976.

Ayala-Grosso et al., "Caspase-3 cleaved spectrin colocalizes with neurofilament-immunoreactive neurons in Alzheimer's disease", Neuroscience, 2006, vol. 141, No. 2, pp. 863-874.
Balakumar et al., "Benfotiamine attenuates nicotine and uric acid-induced vascular endothelial dysfunction in the rat", Pharmacological Research, 2008, vol. 58, pp. 356-363.
Benzie et al., "The Ferric Reducing Ability of Plasma (FRAP) as a Measure of "Antioxidant Power": The FRAP Assay", Analytical Biochemistry, Jan. 1996, vol. 239, No. 1, pp. 70-76.
Bera et al., "Effect of Diashis, a polyherbal formulation, in streptozotocin-induced diabetic male albino rats", International journal of Ayurveda research, Jan.-Mar. 2010, vol. 1, No. 1, pp. 18-24.
Boadi et al., "Effect of Quercetin and Genistein on Copper- and Iron-induced Lipid Peroxidation in Methyl Linolenate", Journal of Applied Toxicology, Apr. 2003, vol. 23, No. 5, pp. 363-369.
Botterweck et al., "Intake of Butylated Hydroxyanisole and Butylated Hydroxytoluene and Stomach Cancer Risk: Results from Analyses in the Netherlands Cohort Study", Food Chemistry and Toxicology, 2000, vol. 38, pp. 599-605.
Boyer et al., "Apple phytochemicals and their health benefits", Nutrition Journal, May 2004, vol. 3, No. 5, pp. 1-15.
Bureau et al., "Neuroanatomical and pharmacological assessment of Fos expression induced in the rat brain by the phosphodiesterase-4 inhibitor 6-(4-pyridylmethyl)-8-(3-nitrophenyl) quinoline", Neuropharmacology, 2006, vol. 51, No. 5. pp. 974-985.
Cao et al. "Oxygen-radical absorbance capacity assay for antioxidants", Free Radical Biology and Medicine, Mar. 1993, vol. 14, Issue 3, pp. 303-311.
Cefarelli et al., "Free-Radical-Scavenging and Antioxidant Activities of Secondary Metabolites from Reddened Cv. Annurca Apple Fruits", Journal of Agricultral and Food Chemistry, Jan. 2006, vol. 54, No. 3, pp. 803-809.
Chinnici et al., "Radical Scavenging Activities of Peels and Pulps from cv. Golden Delicious Apples as Related to their Phenolic Composition", Journal of Agricultural Food Chemistry, Jul. 2004, vol. 52, pp. 4684-4689.
Cowper-Smith et al., "Delayed administration of a potent cyclin dependent kinase and glycogen synthase kinase 3β inhibitor produces long-term neuroprotection in a hypoxia-ischemia model of brain injury", Neuroscience, 2008, vol. 155, No. 3. pp. 864-875.
Da Silva et al., "Quercetin metabolites inhibit copper ion-induced lipid peroxidation in rat plasma", FEBS, Jul. 3, 1998, vol. 430, Issue 3, pp. 405-408.
Drogoudi et al., "Peel and flesh antioxidant content and harvest quality characteristics of seven apple cultivars", Scientia Horticulturae, 2008, vol. 115, No. 2, pp. 149-153.
Eberhardt et al., "Antioxidant activity of fresh apples", Nature, Jun. 22, 2000, vol. 405, pp. 903-904.
Ellington et al., "Atherogenic lipoprotein subprofiling", Advances in Clinical Chemistry, 2008, vol. 46, pp. 295-317.
Erkan et al., "Antioxidant activity of rosemary (Rosmarinus Officinalis L) extract, blackseed (Nigella sativa L.) essential oil, carnosic acid, rosmarinic acid and sesamol", Food Chemistry, 2008, vol. 110, pp. 76-82.
Esterbauer et al., "Chemistry and biochemistry of 4-hydroxynonenal, malonaldehyde and related aldehydes", Free Radical Biology and Medicine, 1991, vol. 11, pp. 81-128.
Fang et al., "Determination of DNA adducts of malonaldehyde in humans: Effects of dietary fatty acid composition", Carcinogenesis, 1996, vol. 17, No. 5, pp. 1035-1040.
Frankel et al., "Antioxidant activity of rosemary extract and its constituents, Carnosic acid, Carnosol and Rosemarinic acid in bulk oil and oil-in-water emulsion", Journal of Agricultural and Food Chemistry, 1996, vol. 44, pp. 131-135.
Friedrich et al., "Investigation of proanthocyanidins by HPLC with electrospray ionization mass spectrometry", European Food Research and Technology, 2000, vol. 211, No. 1, pp. 56-64.
Gerhauser et al. "Cancer chemopreventive potential of apples, apple juice, and apple components", Planta Med, Oct. 2008, vol. 74, No. 13, pp. 1608-1624.

(56) References Cited

OTHER PUBLICATIONS

Gugler et al., "Disposition of Quercetin in Man after Single Oral and Intravenous Doses", European Journal of Clinical Pharmacology, 1975, vol. 9, pp. 229-234.

Haila et al., "Effects of Lutein, Lycopene, Annatto, and γ-Tocopherol on Autoxidation of Triglycerides", Journal of Agricultural and Food Chemistry, Aug. 1996, vol. 44, No. 8, pp. 2096-2100.

Halliwell, et al., "The definition and measurement of antioxidants in biological systems", Free Radical Biology and Medicine, Jan. 1995, vol. 18, No. 1, pp. 125-126.

He et al., "Phytochemicals of apple peels: isolation, structure elucidation, and their antiproliferative and antioxidant activities", Journal of Agricultural and Food Chemistry, Nov. 2008, vol. 56, No. 21, pp. 9905-9910.

Hebb et al., "Targeting Apoptosis to Treat Multiple Sclerosis", Current Drug Discovery Technologies, 2008, vol. 5, pp. 75-77.

Heo et al., "Apple phenolics protect in vitro oxidative stress-induced neuronal cell death", Journal of Food Science, Oct. 28, 2004, vol. 69, No. 9, pp. S357-S360.

Hodges et al., "Improving the thiobarbituric acid-reactive-substances assay for estimating lipid peroxidation in plant tissues containing anthocyanin and other interfering compounds", Planta, 1999, vol. 207, No. 4, pp. 604-611.

Hori et al., "Darbepoetin alfa (Aranesp) improves recognition memory in adult rats that have sustained bilateral ventral hippocampal lesions as neonates or young adults", Neuroscience, 2007, vol. 144, No. 1, pp. 1-7.

Hou et al., "Inhibition of human low density lipoprotein oxidation by flavonols and their glycosides", Chemistry and Physics of Lipids, 2004, vol. 129, pp. 209-219.

Huang et al., "High-Throughput Assay of Oxygen Radical Absorbance Capacity (ORAC) Using a Multichannel Liquid Handling System Coupled with a Microplate Fluorescence Reader in 96-Well Format", Journal of Agricultural and Food Chemistry, Jul. 2002, vol. 50, No. 16, pp. 4437-4444.

Huber et al., "Phenolic profiles and antioxidant properties of apple skin extracts" Journal of Food Science, Nov.-Dec. 2009, vol. 74, No. 9, pp. C693-C700.

International Application No. PCT/CA2011/000623, International Search Report dated Sep. 13, 2011.

International Application No. PCT/CA2011/000623, Written Opinion dated Sep. 13, 2011.

International Application No. PCT/CA2011/050289, International Search Report dated Aug. 4, 2011.

Iqbal et al., "Stabilization of sunflower oil by garlic extract during accelerated storage", Food Chemistry, 2007, vol. 100, No. 1, pp. 246-254.

Jia et al., "Co-administration of berberine and plant stanols synergistically reduces plasma cholesterol in rats", Atherosclerosis, Nov. 2008, vol. 201, No. 1, pp. 101-107.

Joshi, A., "Process development and quality assessment of value-added non-fried apple snacks", ProQuest Dissertations and Theses, Oct. 2008.

Kajitani et al., "Nitric Oxide Synthase Mediates the Ability of Darbepoetin Alfa to Improve the Cognitive Performance of STOP Null Mice", Neuropsychopharmacology, 2010, vol. 35, pp. 1718-1728.

PHENOLIC COMPOSITIONS DERIVED FROM APPLE SKIN AND USES THEREOF

CROSS REFERENCE TO RELATED APPLICATIONS

This application is a continuation application of U.S. patent application Ser. No. 13/696,872 filed Nov. 8, 2012, which is a national phase entry of PCT/CA2011/050289 filed on May 10, 2011, which claims priority to U.S. Provisional Patent Application No. 61/333,091 filed May 10, 2010, which are all incorporated herein by reference.

TECHNICAL FIELD

The disclosure relates to phenolic compositions derived from apple skin and uses thereof in the prevention and treatment diseases and conditions associated with oxidative stress and/or inflammation.

BACKGROUND

Natural plant-based phenolic compounds, such as flavonoids, have received much attention for their potent antioxidant properties. Phenolic compounds are present in many plant sources, such as fruits, vegetables and many herbal or aromatic plants. Given their potent anti-oxidant activities, plant phenolics have been under investigation as health-promoting substances for over 20 years.

Apples are a good dietary source of phenolic compounds. Apple peel has 3- to 6-fold higher flavonoid content than apple flesh and has unique flavonoids, such as quercetin glycosides, not found in the flesh (Wolfe, Wu & Liu, 2003; Wolfe & Liu, 2003).

Apple peel extracts have been shown to possess powerful free radical scavenging activity (Kondo et al., 2002). Various apple peel extracts and methods of making them are described, for example, in US 2005/0147723 A1, US 2006/0172012 A1, U.S. Pat. No. 6,440,410 B1, EP 0 659 347 A1, and Kim et al., 2005. PCT application WO 2009/0767776 A1 to Rupasinghe et al. discloses a crude extract derived from apple peel and its use in preventing oxidation of polyunsaturated fatty acids or lipids in food products.

Oxidative stress induced by reactive oxygen species is linked to a number of human conditions and diseases. Plant-derived antioxidants may therefore provide dietary modulators useful in preventing or treating a number of such diseases, including certain neurodegenerative diseases (Kaur and Kapoor, 2001; Heo et al. 2004). A ubiquitous flavonoid, quercetin 3-O-glucoside (Q3G), was recently suggested to have neuroprotective effects in vitro (Soundararajan et al., 2008). Direct treatment of neuronal cells in vivo is not a likely therapeutic approach however, and there is no indication that apple-derived extracts would have any beneficial effect in vivo.

The costs associated with neurodegenerative disorders are in excess of $20 billion annually in North America. Currently, there are no registered natural products with health claims for protecting against these neurodegenerative disorders. As our overall population ages, there is increased desire to maintain health as well as to use alternative medications derived from natural or biological sources. There is a need for discovery and development of safe and effective natural products to treat, prevent or reduce the risk of oxidative stress-mediated conditions and diseases, including neurodegenerative disorders.

Apple peels are a waste product of the apple processing industry in many countries and therefore represent and attractive resource for value-added health-promoting products. While crude extracts have been prepared, there is a need for more refined compositions having potent antioxidant properties. Extraction of phenolic compounds from plant sources presents challenges, since the phenolic compounds are easily oxidized and degrade under harsh extraction conditions.

SUMMARY OF THE ASPECTS

Compositions rich in biologically active phenolic compounds were derived from the skins of apples and were analyzed for phenolic content and profile. It was demonstrated that the phenolic compositions described herein are protective against neuronal cell death in vitro and brain damage and disability in vivo associated with oxidative stress. The phenolic compositions described herein are expected to be useful in the treatment and/or prevention of diseases or conditions associated with oxidative stress, including certain neurodegenerative diseases. Various non-limiting aspects and embodiments are described below.

In one aspect, there is provided a composition for use in preventing or treating an oxidative-stress mediated disease or condition, the composition comprising a phenolic extract or fraction thereof derived from apple skin. In some embodiments, the phenolic extract or fraction thereof comprises a flavonol component, an anthocyanin component, a dihydrochalcone component, a phenolic acid component, and a flavan-3-ol component.

In some embodiments, the flavonol component comprises quercetin, Q-3-O-paltoside, Q-3-O-rutinoside, Q-3-O-galactoside, Q-3-O-glucoside, Q-3-O-rhamnoside or a combination thereof. In some embodiments, the anthocyanin component comprises cyanidin-3-O-galactoside. In some embodiments, the dihydrochalcone component comprises phloridzin, phloritin or a combination thereof. In some embodiments, the phenolic acid component comprises chlorogenic acid, cafeic acid, ferulic acid, isoferulic acid or a combination thereof. In some embodiments, the flavan-3-ol component comprises epigallocatechin, catechin, epicatechin or a combination thereof.

In one embodiment, the phenolic extract or fraction thereof comprises: a flavonol component comprising quercetin, Q-3-O-paltoside, Q-3-O-rutinoside, Q-3-O galactoside, Q-3-O-glucoside and Q-3-O-rhamnoside; an anthocyanin component comprising cyanidin-3-O-galactoside; a dihydrochalcone component comprising phloridzin and phloritin; a phenolic acid component chlorogenic acid, cafeic acid, ferulic acid and isoferulic acid; and a flavan-3-ol component comprising epigallocatechin, catechin and epicatechin.

In some embodiments, the extract or fraction thereof comprises: from about 10.0% to about 60.0%, from about 15.0% to about 50.0%, from about 20.0% to about 50.0%, from about 20.0% to about 35.0%, from about 20.0% to about 30.0%, from about 20.0% to about 25.0% Q-3-O-galactoside; from about 10.0% to about 60.0%, from about 15.0% to about 50.0%, from about 20.0% to about 50.0%, from about 20.0% to about 40.0%, from about 20.0% to about 35.0%, from about 20.0% to about 30.0%, from about 20.0% to about 25.0%, from about 30.0% to about 35.0% Q-3-O-rhamnoside; from about 1.0% to about 20.0%, from about 5.0% to about 15.0%, from about 7.0% to about 13.0%, from about 5.0% to about 10.0%, from about 10.0% to about 15.0%, Q-3-O-rutinoside; from about 1.0% to about 20.0%, from about 5.0% to about 15.0%, from about 7.0% to about 13.0%, from about 10.0% to about 15.0%, from about 10.0% to about 15.0%, Q-3-O-glucoside; from about 0.5% to about 10.0%, from about 0.5% to about 5.0%, from about 0.5% to about 2.5, from about 0.5% to about 2.0%, from about 1.0% to about 2.0%, from about 2.0% to about 6.0%, from about 3.5% to about 5.5%, from about 4.0% to about 5.0% cyanidin-3-O-galactoside; from about 0.5% to about 10.0%, from about 1.0% to about 10.0%, from about 2.0% to about 10.0%, from about 1.0% to about 5.0%, from about 1.5% to about 4.5%, from about 3.5% to about 7.5%, about 3.0% to about 6.0%, about 3%, about 5% phloridzin; from about 1.0% to about 20.0%, from about 2.0% to about 15.0%, about 5.0% to about 15.0%, from about 2.5% to about 6.5%, from about 8% to about 12.0%, about 4% or about 10% chlorogenic acid; and from about 1.0% to about 20.0%, from about 1.0% to about 15.0%, from about 5.0% to about 15.0%, from about 2.5% to about 10.0%, from about 2.5% to about 6.5%, from about 5.0% to about 10.0%, from about 8.0% to about 10.0% epicatechin.

In some embodiments, the extract or fraction thereof comprises: from about 20.0% to about 30.0% Q-3-O-galactoside; from about 20.0% to about 30.0% Q-3-O-rhamnoside; from about 10.0% to about 15.0%, Q-3-O-rutinoside; from about 10.0% to about 15.0%, Q-3-O-glucoside; from about 2.0% to about 6.0% cyanidin-3-O-galactoside; from about 1.0% to about 5.0%, phloridzin; from about 8% to about 12.0% chlorogenic acid; and from about 5.0% to about 10.0% epicatechin.

In some embodiments, the extract or fraction thereof comprises: from about 20.0% to about 35.0% Q-3-O-galactoside; from about 20.0% to about 35.0% Q-3-O-rhamnoside; from about 5.0% to about 15.0% Q-3-O-rutinoside; from about 5.0% to about 15.0% Q-3-O-glucoside; from about 0.5% to about 2.5 cyanidin-3-O-galactoside; from about 1.0% to about 5.0% phloridzin; from about 5.0% to about 15.0% chlorogenic acid; and from about 5.0% to about 10.0% epicatechin.

In some embodiments, the phenolic extract is obtainable by an aqueous extraction process having the following steps: obtaining a sample of apple skins; treating the skins to inhibit degradation of phenolic compounds; optionally dehydrating the skins and converting the skins to a powder form; extracting the skins one or more times with a food-grade solvent, such as, ethanol; optionally subjecting the skins to sonication during extraction; removing solids to obtain a phenolic extract; optionally concentrating the phenolic extract; optionally removing sugars from the phenolic extract, and optionally concentrating, drying and/or freezing the phenolic extract.

In some embodiments, the fraction is obtainable by fractionation of the phenolic extract using a suitable eluent, followed by selection of a fraction having a high phenolic content. In some embodiments, a fraction having a high flavonol content is selected.

In some embodiments, the fraction is eluted in about 40% to about 60% ethanol. In some embodiments, the fraction is eluted in about 45% to about 50% ethanol.

In some embodiments, the fraction has the following phenolic profile: from about 60.0% to about 95.0% flavonol selected from the group consisting of quercetin (Q), Q-3-O-paltoside, Q-3-O-rutinoside, Q-3-O galactoside, Q-3-O-glucoside, Q-3-O-rhamnoside and combinations thereof; from about 0.5% to about 10.0% cyanidin-3-O-galactoside; from about 1.0% to about 10.0 dihydrochalcone selected from the group consisting of phloridzin, phloritin and combinations thereof; from about 1.0% to about 20.0% phenolic acid selected from the group consisting of chlorogenic acid, cafeic acid, ferulic acid, isoferulic acid and combinations thereof; and from about 1.0% to about 20.0% flavan-3-ol selected from the group consisting of epigallocatechin, catechin, epicatechin and combinations thereof, wherein the percentages are based the total weight of phenolic content of the fraction and wherein the total does not exceed 100%.

In some embodiments, the fraction has the following phenolic profile: from about 70.0% to about 90.0% flavonol selected from the group consisting of quercetin, Q-3-O-paltoside, Q-3-O-rutinoside, Q-3-O-galactoside, Q-3-O-glucoside, Q-3-O-rhamnoside and combinations thereof; from about 0.5% to about 5.0% cyanidin-3-O-galactoside; from about 2.0% to about 10.0% dihydrochalcone selected from the group consisting of phloridzin, phloritin and combinations thereof; from about 2.0% to about 15.0% phenolic acid selected from the group consisting of chlorogenic acid, cafeic acid, ferulic acid, isoferulic acid and combinations thereof; and from about 1.0% to about 15.0% flavan-3-ol selected from the group consisting of epigallocatechin, catechin, epicatechin and combinations thereof.

In some embodiments, the fraction comprises: from about 80.0% to about 90.0% flavonol selected from the group consisting of quercetin, Q-3-O-paltoside, Q-3-O-rutinoside, Q-3-O-galactoside, Q-3-O-glucoside, Q-3-O-rhamnoside and combinations thereof; from about 0.5% to about 2.5% cyanidin-3-O-galactoside; from about 3.5% to about 7.5% dihydrochalcone selected from the group consisting of phloridzin, phloritin and combinations thereof; from about 2.5% to about 6.5% phenolic acid selected from the group consisting of chlorogenic acid, cafeic acid, ferulic acid, isoferulic acid and combinations thereof; and from about 2.5% to about 6.5% flavan-3-ol selected from the group consisting of epigallocatechin, catechin, epicatechin and combinations thereof.

In some embodiments, the fraction comprises: from about 70.0% to about 80.0% flavonol selected from the group consisting of quercetin, Q-3-O-paltoside, Q-3-O-rutinoside, Q-3-O-galactoside, Q-3-O-glucoside, Q-3-O-rhamnoside and combinations thereof; from about 2.0% to about 6.0% cyanidin-3-O-galactoside; from about 1.5% to about 4.5% dihydrochalcone selected from the group consisting of phloridzin, phloritin and combinations thereof; from about 8.0% to about 12.0% phenolic acid selected from the group consisting of chlorogenic acid, cafeic acid, ferulic acid, isoferulic acid and combinations thereof; and from about 8.0% to about 12.0% flavan-3-ol selected from the group consisting of epigallocatechin, catechin, epicatechin and combinations thereof.

In some embodiments, the composition further comprises a pharmaceutically acceptable excipient.

In some embodiments, the disease or condition associated with oxidative stress or inflammation is aging, obesity, autoimmune diseases, such as, arthritis, diabetes, lupus, colitis and Crohn's disease, heart disease, atherosclerosis, stroke, myocardial infarction, retinal degeneration, hearing loss, fragile X syndrome, chronic fatigue syndrome, traumatic brain injury, spinal cord injury, head injury, demyelinating disorders, such as multiple sclerosis, devic's, progressive multifocal leukoencephalopathy, optic neuritis, leukodystrophies, charcot-marie tooth, and guillian-barre syndrome, or oxidative stress-induced neurodegenerative diseases, such as multiple sclerosis, Parkinson's disease and Alzheimer's disease and vascular dementia. The compositions described herein may also be useful in the treatment or prevention of certain oxidative stress-mediated orphan disorders, such as amyotrophic lateral sclerosis (ALS), primary progressive MS, charcot-marie-tooth disease, and spinal muscular atrophy.

In another aspect, there is provided a method of preventing or treating an oxidative-stress mediated disease or condition, comprising administering to a subject an effective amount of a composition as defined herein.

In another aspect, there is provided a method of preventing or treating an oxidative-stress mediated disease or condition, comprising administering to a subject an effective amount of a phenolic extract or fraction thereof derived from apple skin.

In some embodiments, the phenolic extract or fraction thereof is administered to a subject in multiple doses.

In some embodiments, the phenolic extract or fraction thereof is administered orally.

In some embodiments, the phenolic extract or fraction thereof is administered in the form of a concentrate, a liquid, a powder, an emulsion, a suspension, a paste, a gel, a film, a gum, a drop, a tablet, a capsule, a microcapsule, a food additive.

In another aspect, there is provided a fraction of a phenolic apple skin extract, the extract obtainable by an aqueous extraction process, the fraction obtainable by fractionating the extract in a chromatography column using a suitable eluent and selecting a fraction having a high phenolic content, wherein the fraction comprises a flavonol component, an anthocyanin component, a dihydrochalcone component, a phenolic acid component, and a flavan-3-ol component. The fraction has the features as defined above.

In another aspect, there is provided a dietary supplement or natural health product for preventing or reducing damage due to oxidative stress comprising a fraction of as defined herein.

In another aspect, there is provided a functional food or beverage comprising a fraction as defined herein.

In another aspect, there is provided a pharmaceutical composition comprising a fraction as defined herein together with a pharmaceutically acceptable excipient.

In some embodiments, the pharmaceutical composition is formulated for enteral administration, topical administration, parenteral administration, intrapulmonary administration or nasal administration. In some embodiments, the enteral administration is oral administration.

In some embodiments, the pharmaceutical composition is for use in the prevention or treatment of a disease or condition associated with oxidative stress.

In some embodiments, the pharmaceutical composition is for use in the prevention or treatment of a disease or condition associated with inflammation.

In another aspect there is provided, a use of a composition as defined herein the preparation of a medicament for the treatment or prevention of a disease or condition associated with oxidative stress and/or inflammation.

In another aspect there is provided, use of a composition as defined herein for the treatment or prevention of a disease or condition associated with oxidative stress and/or inflammation.

In another aspect there is provided, a commercial package comprising a composition as defined herein together with instructions for use as a dietary supplement or natural health product.

In another aspect there is provided a commercial package comprising the dietary supplement or natural health product as defined herein together with instructions for use in promoting health.

In another aspect there is provided a commercial package comprising a pharmaceutical composition as defined herein together with instructions for use in the use in the treatment or prevention of a disease or condition associated with oxidative stress and/or inflammation.

In another aspect there is provided a food additive comprising a fraction as defined herein.

In another aspect there is provided a cosmetic product comprising a fraction as defined herein.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein.

DETAILED DESCRIPTION

Figure 1:
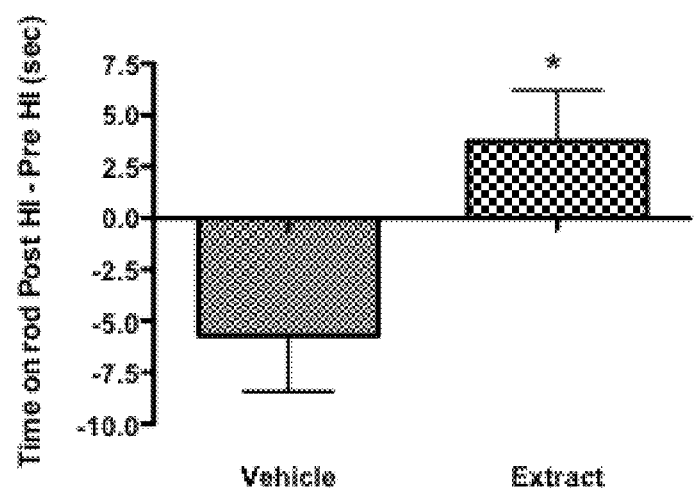
FIG. 1 illustrates that hypoxic-ischemic (HI) brain injury in mice treated with F5 had better motor performance as assessed by the rotarod compared to control mice treated with vehicle.

Apples, particularly apple skins, are a rich source of phenolic compounds, such as flavonoids, which have potent antioxidant potential. Apple skins are a waste product of the apple processing industry (e.g. apple sauce, apple pie) in many countries and are typically available at high quantity and low cost. Therefore, phenolic compounds isolated from apple skin represent an ideal source of natural antioxidants for the food, natural health product, pharmaceutical and cosmetic industries. Since the raw source material is readily available at low cost, an economic benefit is realized which can be passed on to consumers, thereby having the potential to decrease the cost of health care.

The present disclosure relates to phenolic compositions, in particular, phenolic extracts and fractions thereof derived from apple skin, and their use in the prevention or treatment of diseases or conditions associated with oxidative stress and/or inflammation. Also disclosed herein are methods of preparing the phenolic compositions from apple skins. The phenolic compositions are naturally-derived, consumer-friendly compositions, thereby fulfilling a growing desire for natural health-promoting products, such as natural health products or nutriceuticals, dietary supplements, and functional foods. The compositions have potent antioxidant and anti-inflammatory properties making them also suitable for use in pharmaceutical and cosmetic applications.

Based on the results discussed further below, it is expected that the phenolic compositions described herein will have utility in the prevention or treatment of various conditions and diseases associated with oxidative stress or inflammation. With regards to oxidative stress, this hypothesis is supported by the fact that free radical generation has been implicated in numerous human disorders and conditions, and flavonoids are excellent free radical scavengers. Oxidative stress generally refers to excess production of free radicals, which can result from a number of different causes, such as tissue damage, inflammation, and excitotoxicity. The beneficial effects of two exemplary compositions, F4 or F5, were seen at concentrations less than ⅒ that of an anti-oxidant concentration of Vitamin C, thus the beneficial effects of the compositions disclosed herein are not likely entirely due to anti-oxidant effects. There is an emerging view that flavonoids, and their in vivo metabolites, may exert modulatory actions in cells through actions at protein kinase and lipid kinase signalling pathways. Flavonoids, and more recently their metabolites, have been reported to act at phosphoinositide 3-kinase (PI 3-kinase), Akt/protein kinase B (Akt/PKB), tyrosine kinases, protein kinase C (PKC), and mitogen activated protein kinase (MAP kinase) signalling cascades. Inhibitory or stimulatory actions at these pathways are likely to affect cellular function profoundly by altering the phosphorylation state of target molecules and by modulating gene expression (Williams R J et al, 2004). Thus, in addition to being radical scavengers, flavonoids may also modulate various kinase pathways involved in cell stress and cell death. With regard to inflammation, the results demonstrated herein illustrate that the phenolic compositions of the present disclosure are also capable of inhibiting phosphodiesterases and inflammatory cytokine production, indicating that the compositions are effective anti-inflammatory agents as well. The compositions defined herein have unique phenolic profiles and it is believed that synergies between the particular components present in a given fraction may contribute to their potent therapeutic effects.

The phenolic compositions disclosed herein have potential for preventing or treating one or more conditions or diseases associated with oxidative stress or inflammation, including those having components related to apoptosis, necrosis, damage to cerebral vasculature, neuroinflammation, excitotoxicity, and the like. Exemplary diseases and conditions associated with oxidative stress and/or inflammation include, but are not limited to, aging, chronic fatigue syndrome, neurodegenerative disorders, autoimmune disorders, metabolic disorders, and vascular disorders. Neurodegenerative disorders include, for example, Parkinson's disease, Alzheimer's disease, retinal degeneration, hearing loss, fragile X syndrome, chronic fatigue syndrome, traumatic brain injury, spinal cord injury, head injury and demyelinating disorders. Demyelinating disorders include, for example, multiple sclerosis, devic's, progressive multifocal leukoencephalopathy, optic neuritis, leukodystrophies, charcot-marie tooth, and guillian-barre syndrome. Autoimmune disorders include, for example, type I diabetes, rheumatoid arthritis, lupus, colitis and Crohn's disease. Vascular disorders include, for example, stroke, atherosclerosis, myocardial infarction and vascular dementia. Beneficial effects of flavonoids may derive, at least in part, from protection of the cerebral vasculature and microvasculature, such as in stroke, MS, and vascular dementia. Metabolic disorders include, for example, obesity, type II diabetes, and lipid disorders, such as, hypercholesteremia. The compositions described herein may also be useful in the treatment or prevention of certain oxidative stress-mediated orphan disorders, such as amyotrophic lateral sclerosis (ALS), primary progressive MS, charcot-marie-tooth disease, and spinal muscular atrophy. It will be understood that diseases and conditions associated with oxidative stress and/or inflammation may fall into more than one category listed above.

The following section defines various terms and expressions used throughout the instant specification.

The term "phenolic" refers generally to naturally-occurring chemical compounds found in plants having at least one phenol group. As used herein, "phenolic" refers to polyphenolic compounds derived from apples, in particular, flavonoids present in apple skins (see, for example, Table 2a and b). Flavonoids include, but are not limited to, flavonols (e.g. quercetin and various glycosides thereof), anthocyanidins, dihydrochalcones, phenolic acids, and flavan-3-ols (or catechins) Flavonoids are known to scavenge free radicals, inhibit a variety of kinases, reduce lipid peroxidation, inhibit apoptosis, prevent platelet aggregation and exhibit anti-inflammatory effects.

As used herein, "phenolic content" of an extract or fraction thereof refers to monomeric phenolic content and is based on the monomeric phenolic compounds recited in Table 2a and 2b, where the percentage of each compound is calculated based the total weight of the monomeric phenolic content of the composition. The total percentage of the phenolic content does not exceed 100%. The compositions may comprise additional phenolic compounds not recited in Tables 2a and 2b but these are not included for the purpose of determining the percentages used herein.

A "high phenolic content" refers to selection of a fraction having a relatively high phenolic content compared to other fractions isolated, or compared to a crude extract. For example, of 15 fractions analyzed in Tables 2a and 2b, fractions F4 and F5 have relatively high monomeric phenolic content compared to the other fractions. In particular, F4 and F5 have a relatively high flavonol content compared to the other fractions. A "high flavonol content" refers to a fraction that is enriched in flavonols compared to other fractions or compared to a crude extract. Through a process such as fractionation, a fraction may have a higher flavonol content (% flavonol in the total phenolic content) than a crude extract from which is was derived.

A "phenolic extract or fraction thereof" is a flavonoid rich extract prepared from extraction of apple skills, or an enriched fraction isolated therefrom. A desired fraction may be isolated, for example, using column chromatography. The extract or fraction thereof may be further processed to any desired form and, for example, may be in the form of a liquid, a suspension, an emulsion, a solution, or a solid (such as a powder or a lyophilized product). Thus, it will be understood that the term extract or fraction does not necessarily refer to a liquid form of the extract or fraction.

As used herein, the "phenolic profile" of an extract or a fraction refers to the particular combination of phenolic compounds, in particular, flavonoids, in the extract or fraction and their amount relative to each other.

The term "effective amount" is an amount sufficient to achieve a desired outcome in a subject. For treatment, an effective amount is a therapeutically effective amount. The therapeutically effective amount can vary depending, for example, on the disease, disorder, or symptom of the disease or disorder, severity of the disease, disorder, or symptom of the disease or disorder, the age, weight, or health of the patient to be treated, and the judgment of the prescribing physician. An appropriate therapeutically effective amount in any given instance may be ascertained by those skilled in the art or capable of determination by routine experimentation. In some cases, a therapeutically effective amount is an amount sufficient to provide at least about 1 mg/kg/d to about 2000 mg/kg/d, 1 mg/kg/d to about 1500 mg/kg/d or 1 mg/kg/d to about 1000 mg/kg/d, or about 5 mg/kg/d to about 500 mg/kg/d, or about 25 mg/kg/d to about 200 mg/kg/d, or about 10 mg/kg/d to about 100 mg/kg/d, of total phenolic content to the subject. For prevention, an effective amount is a prophylactically effective amount. An effective amount may also be an amount sufficient to promote good heath. The effective amount will depend, at least in part, on the particular use of the phenolic composition (e.g. dietary supplement, functional food, natural health product or pharmaceutical product) and the desired outcome.

The term "oxidative stress" refers generally to an imbalance between the production of reactive oxygen species and a biological system's ability to readily detoxify the reactive intermediates or easily repair the resulting damage. In humans, oxidative stress is implicated in many conditions and diseases, such as aging, arthritis, diabetes, heart disease, atherosclerosis, stroke, myocardial infarction, vascular dementia, retinal degeneration, hearing loss, fragile X syndrome, chronic fatigue syndrome and neurodegenerative disease.

As used herein, the term "disease or condition" refers to a disease, disorder, condition, pathology, or symptom of any of the foregoing. The term "disease" typically refers to an abnormal condition affecting the body of an organism. It is often construed to be a medical condition associated with specific symptoms and signs. As used herein, a "condition" refers to a state of being which is desired to be treated or prevented but which is not typically regarded as a disease, such as aging.

As used herein, the term "treat" or "treating" means to alleviate or eliminate symptoms, either on a temporary or permanent basis, or to slow the appearance of symptoms of a disease or condition, or to slow the development of a disease or condition, or to prolong the period before recurrence of a symptom or negative event associated with a disease or condition. The act of treating may not eliminate symptoms altogether but will provide some relief or improvement to the subject as compared to no treatment.

As used herein, the term "prevent" or "preventing" means to prevent the onset of a disease or condition, or a symptom of a disease or condition, for example, in a population believed to be susceptible to the disease or condition.

As used herein, the term "excipients" refers to carriers, diluents, additives and the like, having substantially no pharmacological activity. The excipients are preferably "pharmaceutically acceptable" referring to excipients which are nontoxic when administered to a subject in an amount sufficient to provide a desired effect and which do not destroy the biological activity of the phenolic extract or fraction thereof.

As sued herein, a "subject" refers to mammals, in particular, humans, domesticated animals (e.g. pets), laboratory animals, and livestock.

A "dose" refers to the amount of active agent to be administered to a subject in a given unit(s) of a dosage form. The dose required to achieve efficacy can vary depending on, for example, the disease or condition to be treated, the dosage form, and the route of administration.

As used herein, "food" encompasses any item consumable by humans or animals, for example, for nutrition, health or pleasure, and includes both foods and beverages.

Terms of degree such as "substantially", "about" and "approximately" as used herein mean a reasonable amount of deviation of the modified term such that the end result is not significantly changed.

As used herein, the term "about" in association with a numeric value or range refers to a variation of +/−5%.

When introducing elements disclosed herein, the articles "a", "an", "the", and "said" are intended to mean that there are one or more of the elements.

The terms "comprising", "having", "including" are intended to be open-ended and mean that there may be additional elements other than the listed elements.

Reference is now made in detail to embodiments of the present disclosure. The disclosed embodiments are not intended to be limiting of the claims. To the contrary, the claims are intended to cover alternatives, modifications, and equivalents.

In one broad aspect, there is provided herein a composition for use in preventing or treating a disease or condition associated with oxidative stress and/or inflammation. The composition comprises a phenolic extract or fraction thereof derived from apple skin.

The flavonoid-rich phenolic extract or fraction thereof comprises a flavonol component, an anthocyanin component, a dihydrochalcone component, a phenolic acid component, and a flavan-3-ol component. The components are used in measuring total phenolic content of the extract or fraction thereof.

The flavonol component may comprise quercetin, Q-3-O-paltoside, Q-3-O-rutinoside, Q-3-O-galactoside, Q-3-O-glucoside, Q-3-O-rhamnoside or a combination thereof. In one embodiment, wherein the flavonol component comprises quercetin, Q-3-O-paltoside, Q-3-O-rutinoside, Q-3-O-galactoside, Q-3-O-glucoside and Q-3-O-rhamnoside.

The anthocyanin component may comprise cyanidin-3-O-galactoside.

The dihydrochalcone component may comprise phloridzin, phloritin or a combination thereof. In one embodiment, the dihydrochalcone component comprises phloridzin and phloritin.

The phenolic acid component may comprise chlorogenic acid, cafeic acid, ferulic acid, isoferulic acid or a combination thereof. In one embodiment, wherein the phenolic acid component comprises chlorogenic acid, cafeic acid, ferulic acid and isoferulic acid.

The flavan-3-ol component may comprises epigallocatechin, catechin, epicatechin or a combination thereof. In one embodiment, the flavan-3-ol component comprises epigallocatechin, catechin and epicatechin.

In one embodiment, the phenolic extract or fraction thereof comprises: a flavonol component comprising quercetin, Q-3-O-paltoside, Q-3-O-rutinoside, Q-3-O-galactoside, Q-3-O-glucoside and Q-3-O-rhamnoside; an anthocyanin component comprising cyanidin-3-O-galactoside; a dihydrochalcone component comprising phloridzin and phloritin; a phenolic acid component chlorogenic acid, cafeic acid, ferulic acid and isoferulic acid; and a flavan-3-ol component comprising epigallocatechin, catechin and epicatechin.

The phenolic extract is obtainable by an aqueous extraction process. An exemplary process has the following steps: obtaining a sample of apple skins; treating the skins to inhibit degradation of phenolic compounds; optionally dehydrating the skins and converting the skins to a powder form; extracting the skins one or more times with a food-grade solvent, such as, ethanol; optionally subjecting the skins to sonication during extraction; removing solids to obtain a phenolic extract; optionally concentrating the phenolic extract; optionally removing sugars from the phenolic extract, and optionally concentrating, drying and/or freezing the phenolic extract.

In some embodiments, the extract is further purified, for instance using column chromatography (e.g. C18 column chromatography). Purification may be performed to remove additional components from the crude extract, for example, highly lipophilic components. Ethanol or another suitable food-grade solvent can be used as the eluent, for example, 80%, 85%, 90%, 95% or 100% ethanol.

In some embodiments, the extract (crude or purified) is subjected to fractionation to obtain eluted fractions. Fractionization may be carried out using any suitable method, such as column chromatography. Preferably the selected fraction has a relatively high phenolic content compared to other fractions potentially isolated. An eluted fraction may comprise a unique combination and/or concentration of individual components compared to the crude extract and compared to other fractions (i.e. a unique phenolic profile). Thus, different fractions may exhibit different biological effects. In addition, each fraction prepared may contain unidentified active compounds that may contribute to the biological activity. Synergies may be seen between the active components. In some embodiments, fractions enriched for flavonols are selected.

In some embodiments, the fraction is obtainable by fractionation of the phenolic extract in a chromatography column using a suitable eluent. In some embodiment, the fraction is obtained by fractionation of the phenolic extract in a chromatography column using a suitable eluent. Any suitable eluent may be used, for example, ethanol or another suitable food-grade eluent. In some embodiments, the chromatography used is flash chromatography with a C18 column using a polymeric sorbent.

In some embodiments, the fractionation step is followed by analysis of the fractions and selection of one or more fractions having a high phenolic content. Phenolic content may be measured by any suitable means. Is some embodiments, the phenolic content is measured as described in Example 1. In some embodiments, the selected fraction has a high phenolic content of greater than about 7000 mg/ml, greater than about 9000 mg/ml, greater than about 10000 mg/mL, greater than about 11000 mg/mL, greater than about 12000 mg/mL, or greater than about 13000 mg/mL based on an elution volume of 800 ml.

Is some embodiments, the selected fraction has a high flavonol content for example, a flavonol content of greater than about 60%, 65%, 70%, 75%, 80%, 85%, 90%, 95% based the total phenolic content of the fraction. The flavonol content may be relatively high compared to other fractions and/or compared to a crude extract.

In some embodiments, the selected fraction is a fraction or fractions that elute in about 40% to about 60% ethanol, as described in Example 1. For example, one or more fractions eluting in ethanol concentrations may be removed prior to collecting one or more fractions that elute between about 40% to about 60% ethanol. In some embodiments, the fraction is eluted in about 45% to about 50% ethanol. In one embodiment, the fraction is eluted in about 45% ethanol. In another embodiment, the fraction is eluted in about 50% ethanol.

In some embodiments, the composition comprises fraction F4 or F5 of Table 2a, which may optionally be diluted, concentrated or dried prior to use. In some embodiments, F4 and F5 are combined to form a single flavonol-rich fraction that elutes between about 45% to about 50% ethanol.

In some embodiments, the extract or fraction thereof comprises from about 60.0% to about 95.0%, from about 70.0% to about 90.0%, from about 70.0% to about 80.0%, from about 80.0% to about 90.0% flavonol. In some embodiments, the extract or fraction thereof comprises from greater than about 60.0%, 70%, 75%, 80%, 85%, 90% or 95.0% flavonol. This is higher than the crude extract, which was found to have a flavonol concentration of only about 50%. In some embodiments, the flavonol is selected from the group consisting of quercetin, Q-3-O-paltoside, Q-3-O-rutinoside, Q-3-O-galactoside, Q-3-O-glucoside, Q-3-O-rhamnoside and combinations thereof.

In some embodiments, the extract or fraction thereof comprises from about 10.0% to about 60.0%, from about 15.0% to about 50.0%, from about 20.0% to about 50.0%, from about 20.0% to about 35.0%, from about 20.0% to about 30.0%, from about 20.0% to about 25.0% Q-3-O-galactoside.

In some embodiments, the extract or fraction thereof comprises from about 10.0% to about 60.0%, from about 15.0% to about 50.0%, from about 20.0% to about 50.0%, from about 20.0% to about 40.0%, from about 20.0% to about 35.0%, from about 20.0% to about 30.0%, from about 20.0% to about 25.0%, from about 30.0% to about 35.0% Q-3-O-rhamnoside.

In some embodiments, the extract or fraction thereof comprises from about 1.0% to about 20.0%, from about 5.0% to about 15.0%, from about 7.0% to about 13.0%, from about 5.0% to about 10.0%, from about 10.0% to about 15.0%, Q-3-O-rutinoside.

In some embodiments, the extract or fraction thereof comprises from about 1.0% to about 20.0%, from about 5.0% to about 15.0%, from about 7.0% to about 13.0%, from about 10.0% to about 15.0%, from about 10.0% to about 15.0%, Q-3-O-glucoside.

In some embodiments, the extract or fraction thereof comprises from about 0.5% to about 10.0%, from about 0.5% to about 5.0%, from about 0.5% to about 2.5, from about 0.5% to about 2.0%, from about 1.0% to about 2.0%, from about 2.0% to about 6.0%, from about 3.5% to about 5.5%, from about 4.0% to about 5.0% cyanidin-3-O-galactoside.

In some embodiments, the extract or fraction thereof comprises from about 0.5% to about 10.0%, from about 1.0% to about 10.0%, from about 2.0% to about 10.0%, from about 1.5% to about 4.5%, from about 3.5% to about 7.5%, about 3.0% to about 6.0%, about 3%, about 5% dihydrochalcone. In some embodiments, the dihydrochalcone is selected from the group consisting of phloridzin, phloritin and combinations thereof. In some embodiments, phloridzin represents a major proportion of dihydrochalcone in the composition, for example, greater than 99% phloridzin (300:1, 500:1, 700:1).

In some embodiments, the extract or fraction thereof comprises from about 0.5% to about 10.0%, from about 1.0% to about 10.0%, from about 2.0% to about 10.0%, from about 1.5% to about 4.5%, from about 3.5% to about 7.5%, about 3.0% to about 6.0%, about 3%, about 5% phloridzin.

In some embodiments, the extract or fraction thereof comprises from about 1.0% to about 20.0%, from about 2.0% to about 15.0%, from about 2.5% to about 6.5%, from about 8% to about 12.0% phenolic acid. In some embodiments, the phenolic acid is selected from the group consisting of chlorogenic acid, cafeic acid, ferulic acid, isoferulic acid and combinations thereof. In some embodiments, chlorogenic acid represents a major proportion of phenolic acid in the composition, for example, greater than 85%, greater than 90%, greater than 95%.

In some embodiments, the extract or fraction thereof comprises from about 1.0% to about 20.0%, from about 2.0% to about 15.0%, from about 2.5% to about 6.5%, from about 8% to about 12.0%, about 4% or about 10% chlorogenic acid.

In some embodiments, the extract or fraction thereof comprises from about 1.0% to about 20.0%, from about 1.0% to about 15.0%, from about 2.5% to about 6.5%, from about 8.0% to about 12.0% flavan-3-ol. In some embodiments, the flavan-3-ol is selected from the group consisting of epigallocatechin, catechin, epicatechin and combinations thereof.

In some embodiments, the extract or fraction thereof comprises from about 1.0% to about 20.0%, from about 1.0% to about 15.0%, from about 2.5% to about 10.0%, from about 2.5% to about 6.5%, from about 8.0% to about 10.0% epicatechin.

In some embodiments, the fraction has the following phenolic profile: from about 60.0% to about 95.0% flavonol selected from the group consisting of quercetin, Q-3-O-paltoside, Q-3-O-rutinoside, Q-3-O-galactoside, Q-3-O-glucoside, Q-3-O-rhamnoside and combinations thereof; from about 0.5% to about 10.0% cyanidin-3-O-galactoside; from about 1.0% to about 10.0% dihydrochalcone selected from the group consisting of phloridzin, phloritin and combinations thereof; from about 1.0% to about 20.0% phenolic acid selected from the group consisting of chlorogenic acid, cafeic acid, ferulic acid, isoferulic acid and combinations thereof; and from about 1.0% to about 20.0% flavan-3-ol selected from the group consisting of epigallocatechin, catechin, epicatechin and combinations thereof, wherein the percentages are based the total weight of phenolic content of the fraction and wherein the total does not exceed 100%.

In one embodiment, the fraction has the following phenolic profile: from about 70.0% to about 90.0% flavonol selected from the group consisting of quercetin, Q-3-O-paltoside, Q-3-O-rutinoside, Q-3-O-galactoside, Q-3-O-glucoside, Q-3-O-rhamnoside and combinations thereof; from about 0.5% to about 5.0% cyanidin-3-O-galactoside; from about 2.0% to about 10.0% dihydrochalcone selected from the group consisting of phloridzin, phloritin and combinations thereof; from about 2.0% to about 15.0% phenolic acid selected from the group consisting of chlorogenic acid, cafeic acid, ferulic acid, isoferulic acid and combinations thereof; and from about 1.0% to about 15.0% flavan-3-ol selected from the group consisting of epigallocatechin, catechin, epicatechin and combinations thereof.

In one embodiment, the fraction comprises: from about 80.0% to about 90.0% flavonol selected from the group consisting of quercetin, Q-3-O-paltoside, Q-3-O-rutinoside, Q-3-O-galactoside, Q-3-O-glucoside, Q-3-O-rhamnoside and combinations thereof; from about 0.5% to about 2.5% cyanidin-3-O-galactoside; from about 3.5% to about 7.5% dihydrochalcone selected from the group consisting of phloridzin, phloritin and combinations thereof; from about 2.5% to about 6.5% phenolic acid selected from the group consisting of chlorogenic acid, cafeic acid, ferulic acid, isoferulic acid and combinations thereof; and from about 2.5% to about 6.5% flavan-3-ol selected from the group consisting of epigallocatechin, catechin, epicatechin and combinations thereof. This would, for example, encompass fraction F5 in Table 2a.

In one embodiment, the fraction comprises: from about 70.0% to about 80.0% flavonol selected from the group consisting of quercetin, Q-3-O-paltoside, Q-3-O-rutinoside, Q-3-O-galactoside, Q-3-O-glucoside, Q-3-O-rhamnoside and combinations thereof; from about 2.0% to about 6.0% cyanidin-3-O-galactoside; from about 1.5% to about 4.5% dihydrochalcone selected from the group consisting of phloridzin, phloritin and combinations thereof; from about 8.0% to about 12.0% phenolic acid selected from the group consisting of chlorogenic acid, cafeic acid, ferulic acid, isoferulic acid and combinations thereof; and from about 8.0% to about 12.0% flavan-3-ol selected from the group consisting of epigallocatechin, catechin, epicatechin and combinations thereof. This would, for example, encompass fraction F4 of Table 2a.

In some embodiments, the extract or fraction thereof comprises: from about 10.0% to about 60.0%, from about 15.0% to about 50.0%, from about 20.0% to about 50.0%, from about 20.0% to about 35.0%, from about 20.0% to about 30.0%, from about 20.0% to about 25.0% Q-3-O-galactoside; from about 10.0% to about 60.0%, from about 15.0% to about 50.0%, from about 20.0% to about 50.0%, from about 20.0% to about 40.0%, from about 20.0% to about 35.0%, from about 20.0% to about 30.0%, from about 20.0% to about 25.0%, from about 30.0% to about 35.0% Q-3-O-rhamnoside; from about 1.0% to about 20.0%, from about 5.0% to about 15.0%, from about 7.0% to about 13.0%, from about 5.0% to about 10.0%, from about 10.0% to about 15.0%, Q-3-O-rutinoside; from about 1.0% to about 20.0%, from about 5.0% to about 15.0%, from about 7.0% to about 13.0%, from about 10.0% to about 15.0%, from about 10.0% to about 15.0%, Q-3-O-glucoside; from about 0.5% to about 10.0%, from about 0.5% to about 5.0%, from about 0.5% to about 2.5, from about 0.5% to about 2.0%, from about 1.0% to about 2.0%, from about 2.0% to about 6.0%, from about 3.5% to about 5.5%, from about 4.0% to about 5.0% cyanidin-3-O-galactoside; from about 0.5% to about 10.0%, from about 1.0% to about 10.0%, from about 2.0% to about 10.0%, from about 1.0% to about 5.0%, from about 1.5% to about 4.5%, from about 3.5% to about 7.5%, about 3.0% to about 6.0%, about 3%, about 5% phloridzin; from about 1.0% to about 20.0%, from about 2.0% to about 15.0%, about 5.0% to about 15.0%, from about 2.5% to about 6.5%, from about 8% to about 12.0%, about 4% or about 10% chlorogenic acid; and from about 1.0% to about 20.0%, from about 1.0% to about 15.0%, from about 5.0% to about 15.0%, from about 2.5% to about 10.0%, from about 2.5% to about 6.5%, from about 5.0% to about 10.0%, from about 8.0% to about 10.0% epicatechin.

In some embodiments, the extract or fraction thereof comprises: from about 20.0% to about 30.0% Q-3-O-galactoside; from about 20.0% to about 30.0% Q-3-O-rhamnoside; from about 10.0% to about 15.0%, Q-3-O-rutinoside; from about 10.0% to about 15.0%, Q-3-O-glucoside; from about 2.0% to about 6.0% cyanidin-3-O-galactoside; from about 1.0% to about 5.0%, phloridzin; from about 8% to about 12.0% chlorogenic acid; and from about 5.0% to about 10.0% epicatechin.

In some embodiments, the extract or fraction thereof comprises: from about 20.0% to about 35.0% Q-3-O-galactoside; from about 20.0% to about 35.0% Q-3-O-rhamnoside; from about 5.0% to about 15.0% Q-3-O-rutinoside; from about 5.0% to about 15.0% Q-3-O-glucoside; from about 0.5% to about 2.5 cyanidin-3-O-galactoside; from about 1.0% to about 5.0% phloridzin; from about 5.0% to about 15.0% chlorogenic acid; and from about 5.0% to about 10.0% epicatechin.

The percentages of phenolic compounds in the extract or fraction thereof are based the total weight of monomeric phenolic compounds quantified in the extract or fraction thereof and do not exceed 100%.

In some embodiments, the phenolic content comprises from about 5000 to about 15000 mg/L flavonol selected from the group consisting of quercetin, Q-3-O-paltoside, Q-3-O-rutinoside, Q-3-O-galactoside, Q-3-O-glucoside, andQ-3-O-rhamnoside; from about 1 to about 1000 mg/L cyanidin-3-O-galactoside; from about 100 to about 1000 mg/L dihydrochalcone selected from the group consisting of phloridzin and phloritin; from about 100 to about 2000 mg/L phenolic acid selected from the group consisting of chlorogenic acid, cafeic acid, ferulic acid and isoferulic acid; and from about 100 to about 2000 mg/L flavan-3-ol selected from the group consisting of epigallocatechin, catechin and epicatechin. This would include, for example, various compositions made according to the method disclosed in Example 1. Amounts are based on an original elution volume of 800 mL as described in Example 1.

In some embodiments, the phenolic content comprises from about 8000 to about 13000 mg/L flavonol selected from the group consisting of quercetin, Q-3-O-paltoside, Q-3-O-rutinoside, Q-3-O-galactoside, Q-3-O-glucoside, and Q-3-O-rhamnoside; from about 80 to about 700 mg/L cyanidin-3-O-galactoside; from about 300 to about 900 mg/L dihydrochalcone selected from the group consisting of phloridzin and phloritin; from about 400 to about 1600 mg/L phenolic acid selected from the group consisting of chlorogenic acid, cafeic acid, ferulic acid and isoferulic acid; and from about 500 to about 1500 mg/L flavan-3-ol selected from the group consisting of epigallocatechin, catechin and epicatechin.

In some embodiments, the phenolic content comprises from about 10000 to about 12000 mg/L flavonol selected from the group consisting of quercetin, Q-3-O-paltoside, Q-3-O-rutinoside, Q-3-O-galactoside, Q-3-O-glucoside, and Q-3-O-rhamnoside; from about 100 to about 200 mg/L cyanidin-3-O-galactoside; from about 700 to about 800 mg/L dihydrochalcone selected from the group consisting of phloridzin and phloritin; from about 500 to about 600 mg/L phenolic acid selected from the group consisting of chlorogenic acid, cafeic acid, ferulic acid and isoferulic acid; and from about 600 to about 700 mg/L flavan-3-ols selected from the group consisting of epigallocatechin, catechin and epicatechin.

Mass spectrometry analysis indicates that the major flavonoid components of exemplary fractions F4 and F5 are quercetin-3-O-glucoside, quercetin-3-O-galactoside, quercetin-3-O-rhamnoside, quercetin-3-O-rutinoside, epicatechin, chlorogenic acid and phloridzin.

In some embodiments, the phenolic content comprises from about 80.0% to about 90.0% flavonol selected from the group consisting of Q-3-O-rutinoside, Q-3-O-galactoside, Q-3-O-glucoside, Q-3-O-rhamnoside and combinations thereof; from about 1.0% to about 2.0% cyanidin-3-O-galactoside; from about 4.5% to about 6.5% phloridzin; from about 2.5% to about 4.5% chlorogenic acid; and from about 2.5% to about 5.5% epicatechin. In some embodiments, this would include, for example, Fraction F5 of Table 2a.

In one embodiment, the fraction comprises around 70.0% to about 80.0% flavonol selected from the group consisting of Q-3-O-rutinoside, Q-3-O-galactoside, Q-3-O-glucoside, Q-3-O-rhamnoside and combinations thereof; about 4.0% to about 6.0% cyanidin-3-O-galactoside; from about 2.0% to about 4.0% phloridzin; from about 8.0% to about 12.0% chlorogenic acid; and from about 6.0% to about 10.0% epicatechin. In some embodiments, this would include, for example, Fraction F4 of Table 2a.

In some embodiments the, composition further comprises one or more excipients, preferably physiologically acceptable or pharmaceutically acceptable excipients. Suitable excipients are known to those of skill in the art and will be dependent on the dosage from being made, e.g. a natural health product versus a pharmaceutical. It will be understood that other active ingredients may be included in the composition, such as food ingredients and other medicines.

The extract or fraction thereof may be present in a composition or dosage form in any suitable amount that will achieve the desired therapeutic, prophylactic, or health-promoting effect. For instance, the extract or fraction thereof may be present in an amount of about 0.1 wt % to about 99.9 wt %, about 1 wt % to about 85 wt %, about 1 wt % to about 60 wt %, about 1 wt % to about 50 wt %, about 1 wt % to about 40 wt %, about 1 wt % to about 30 wt %, about 5 wt % to about 65 wt %, about 5 wt % to about 30 wt %, about 10 wt % to about 30 wt % of the composition.

In another aspect, there is provided a process for extracting phenolic compounds from apple skins to provide a crude extract and further fractionating the crude extract to provide compositions having unique phenolic profiles.

The phenolic extract is obtainable by an aqueous extraction process having the following steps: obtaining a sample of apple skins; treating the skins to inhibit degradation of phenolic compounds; optionally dehydrating the skins and converting the skins to a powder form; extracting the skins one or more times with a food-grade solvent, such as, ethanol; optionally subjecting the skins to sonication during extraction; removing solids to obtain a phenolic extract; optionally concentrating the phenolic extract; optionally removing sugars from the phenolic extract, and optionally concentrating, drying and/or freezing the phenolic extract. From such a process, a crude extract may be obtained.

In some embodiments, the crude phenolic extract is purified, for example, using column chromatography, for example, chromatography using a C18 column with ethanol, e.g. 80-100% ethanol, as an eluent. Other eluents may also be sued.

One or more fractions may be obtainable by fractionation of the phenolic extract in a chromatography column using a suitable eluent, or other suitable method, followed by selection of a fraction having a high phenolic content, in particular, a high flavonol content. Thus, in some embodiments, the process further comprises subjecting the crude extract to fractionation to obtain eluted fractions; and optionally concentrating, drying and/or freezing the fractions.

In some embodiments, the eluent is ethanol and the chromatography is flash chromatography with a C18 column using a polymeric sorbent.

In some embodiments, fractions having a high phenolic content, in particular, a high flavonol content, are eluted in about 40% to about 60% ethanol. In one embodiment, the fraction is eluted in about 45% to about 50% ethanol. In one embodiment, the fraction is eluted in about 45% ethanol, such as, for example, fraction F4 in Table 2a. In one embodiment, the fraction is eluted in about 50% ethanol, such as, for example, fraction F5 in Table 2a.

The step of treating the skins to inhibit degradation of phenolic compounds may also be carried out by any suitable method, e.g. blanching or salt treatment.

In some embodiments, the step of treating the skins to inhibit degradation of phenolic compounds is carried out by treating the skins (whether dehydrated or not) in a salt solution, for example 1 to 10% calcium chloride ($CaCl_2$) solution, or 1% to 5% $CaCl_2$, e.g. 2% $CaCl_2$, shortly after peeling the fruit, for example, within 10 minutes of peeling, to thereby preserve the antioxidant compounds present in the skins. In some embodiments, the skins are soaked in a salt solution at a temperature of about 40° C. to about 100° C., 50° C. to about 70° C., in particular at about 55° C., for about 5 to about 60 minutes, e.g. 10 minutes.

The peels soaked in salt solution may be extracted directly or freeze-dried for storage and/or transport.

The skins may be ground into a slurry, for example, using an Ursher Mill. In some embodiments, the peels are dehydrated. For example, salt soaked apple peels may be dried in an oven with air circulation at a temperature of about 50° C. to about 70° C., in particular at about 60±2° C., for at least about 24 hours, or about 24 to 72 hours, e.g. about 48 hours.

In some embodiments, dehydrated peels are converted into a fine powder, for example, using mechanical grinding means, such as a coffee grinder or an industrial equivalent. The powdered skins may be used directly or may be frozen for later use.

The skins are extracted using a food-grade solvent. Any suitable solvent may be used, including but not limited to, 40% to 100% methanol or ethanol, e.g. 95% to 100%. In some embodiments, the solvent is 95% to 100% ethanol.

The extraction process is preferably aided by sonication or similar mechanism for disrupting the skins. The conditions to extract the phenolic compounds into the solvent may comprise sonicating for a sufficient period of time, for example, about 5 minutes to 2 hours, or about 10 minutes to about 30 minutes, e.g. 10 or 15 minutes, to release the phenolic compounds into the solvent. An ultrasonication bath or the like may be used.

The extraction step may be repeated as desired. In some embodiments, the extraction step is preformed twice.

Following extraction, solids may be removed by any suitable method, for example, centrifugation or filtration.

The crude extract may optionally be concentrated, for example, to about 1% to about 50%, to about 5% to about 20%, e.g. about 10%, original volume. In some embodiments, the crude extract may be reduced to dryness to provide a solid concentrate, which may be later reconstituted in a suitable medium for use or for fractionation.

The crude extract comprising phenolic compounds may optionally be treated under conditions to remove sugar compounds. The sugars may be removed, for example, by chromatography, for example, flash column chromatography. The column may, for example, be flushed with water one or more times, e.g. two or three times, to remove the sugars. In another embodiment, the solid support or stationary phase in the column is a $C_{18}$ resin or any other support that absorbs hydrophobic compounds (for example, Amberlite XAD 16 or Sorbent SP207-05). The removal of sugar from the crude extract may be monitored, for example, by measuring the Brix value of wash water using a refractometer. In some embodiments, the Brix value is monitored until it reaches less than 5%, e.g. less than 1%, and then the washing step is terminated.

The crude extract comprising phenolic compounds may optionally be treated under conditions to remove lipids, carontenoids, chlorophylls and/or proanthocyanidins (suitable techniques are described, for example, in Huber and Ruphasinghe, 2009).

The crude extract may then be subjected to fractionation to obtain eluted fractions having unique combinations of phenolic compounds, or unique phenolic profiles. The fractions may also contain other agents besides the phenolic compounds. The methods, reagents and conditions employed can affect the constitution of the individual fractions and, once a desirable fraction is obtained, should be controlled for consistency from batch to batch.

Fractionation may be performed, for example, using flash chromatography using a polymeric sorbent. One example of a suitable polymeric sorbent is Sorbent SP207-05 Sepabeads resin brominated styrenic adsorbent; particle size 250 μm, surface area 630 $m^2$/g. In some embodiments, the column contains about 500 to about 800 g, e.g. 600 g, sorbent.

The phenolic compounds may be eluted using any suitable solvent and elution protocol. In some embodiments, the phenolic compounds are eluted using a lower alcohol, such as, methanol, ethanol or propanol. In some embodiments, the eluent is a food-grade lower alcohol. In some embodiments, the phenolic compounds are eluted using a step gradient of ethanol (see Table 1). The eluted fractions may optionally be dried, diluted or concentrated. The eluted fractions may be concentrated, for example, using evaporation techniques, such as rotary evaporation at, for example, 20° C. to 60° C., e.g. 45° C. The eluted fractions may be evaporated to about less than 5%, e.g. about 2.5%, original elution volume. The concentrated or dried samples may later be resuspended in a suitable medium, such as water or other aqueous medium.

In some embodiments, the process of preparation comprises: obtaining a sample of apple skins; treating the skins with a $CaCl_2$ solution shortly after (e.g. within 10 minutes) peeling to inhibit degradation of phenolic compounds; dehydrating the skins and grinding the dried skins to a powder; extracting the powder at least twice with ethanol and subjecting the suspension to sonication during each extraction step; removing solids by centrifugation or equivalent method to obtain a crude phenolic extract; concentrating the crude extract to about 10% original volume; removing sugars from the concentrated crude extract until the Brix value is less than about 1%; subjecting the crude extract to step-gradient fractionation with ethanol on a C-18 chromatography column according to the schedule below to obtain eluted fractions:

| Fraction Number | Percent ethanol |
| --- | --- |
| F1 | 20% |
| F2 | 30% |
| F3 | 40% |
| F4 | 45% |
| F5 | 50% |
| F6 | 55% |
| F7 | 60% |
| F8 | 65% |
| F9 | 70% |
| F10 | 75% |
| F11 | 80% |
| F12 | 90% |
| F13 | 100% |
| F14 | 100% |
| F15 | 100% | selecting eluted fractions F4 and/or F5; and optionally concentrating or drying the selected fractions prior to use. In some embodiments, a fraction having a high phenolic content is selected. In some embodiments, a fraction having a high flavonol content is selected, in particular high quercetin glycosides.

In some embodiments, F4 is selected.

In some embodiments, F5 is selected.

In some embodiments, the treating step involves subjecting the skins to a solution of $CaCl_2$ in water (w/v) at about 55° C. for about 10 minutes. The solution of $CaCl_2$ may for example be about 1%-about 10%, about 1%-about 5%, or about 2% $CaCl_2$.

In some embodiments, the skins are dried at about 60° C.±2° C., for about 48 h, or until dry, prior to being ground to a powder.

In some embodiments, the extraction step is carried out by sonicating the powder in a ratio of 200 g powder to 1 L ethanol two times for 15 minutes with 10 minute interval resulting in a crude extract having a ratio of 200 g powder to 2 L ethanol.

In some embodiments, the crude extract is concentrated using a rotary evaporation system until the original volume is reduced to about 10%.

In some embodiments, the fractionation is carried out using flash chromatography using a polymeric sorbent.

In some embodiments, the sugars are removed by washing the column with 2 to 3 times bed volume of water while monitoring the Brix value of the water exiting the column.

In some embodiments, the step-gradient fractionation is carried out with 800 ml ethanol solution for each fraction.

In some embodiments, the selected fractions are concentrated to about 2.5% of the original elution volume.

In some embodiments, the composition comprises eluted fraction F5 which may optionally be diluted, dried or concentrated.

In some embodiments, the composition comprises eluted fraction F4 which may optionally be diluted, dried or concentrated.

In another aspect, there is provided a dietary supplement or natural health product for reducing or preventing oxidative stress comprising a phenolic composition as described herein. In some embodiments, the dietary supplement or natural health product is in the form of a concentrate, a liquid, a powder, an emulsion, a suspension, a film, a paste, a gel, a gum, a drop, a tablet, a capsule, a microcapsule or a food additive.

There is also provided a dietary supplement or natural health product for preventing or reducing damage due to oxidative stress comprising a fraction as described herein.

In another aspect, there is provided a functional food or beverage comprising a phenolic composition as described herein. Various functional food and beverage formats are known in the industry.

In another aspect, there is provided a method of preventing or treating a disease or condition associated with oxidative stress and/or inflammation, comprising administering to a subject an effective amount of a composition as described herein comprising a phenolic extract or fraction thereof derived from apple skin.

Compositions described herein were shown to reduce neuron death due to oxygen glucose deprivation in vitro and to reduce brain injury and disability in vivo in animal models of diseases and conditions mediated by oxidative stress and inflammation, including neuroinflammation, excitotoxicity, apoptosis, necrosis and/or autoimmunity, such as stroke and multiple sclerosis. The compositions disclosed herein are therefore believed to be useful in preventing or treating a disease or condition associated with oxidative stress and/or inflammation, including neuroinflammation, excitotoxicity, apoptosis, necrosis and/or autoimmunity. The compositions disclosed herein are also believed to be useful in preventing or treating neuron cell death due to oxidative stress, neuroinflammation, excitotoxicity, apoptosis, necrosis and/or autoimmunity.

Without wishing to be bound by theory, at least the following can be noted from the examples. With respect to the oxygen-glucose deprivation (OGD) experiment on cortical neurons, glutamate antagonists are known to be protective. If therefore possible that F4 reduced the detrimental effects of OGD by preventing excitotoxicity and oxidative stress, perhaps by increasing resistance to this cause of neuronal cell death by stabilizing calcium overload. With respect to EAE (animal model of MS), neuroinflammation resulting from autoimmune mechanism is the primary cause of paralysis, thus F4 may be blocking this type of injury. In hypoxia-ischemia (HI)-induced brain injury, neuroinflammation, excitotoxicity, as well oxidative stress are all at play. The compositions disclosed herein were also shown to inhibit phosphodiesterase IV and inflammatory cytokine production. The compositions disclosed herein may therefore also improve cognition by reducing neuroinflammation and oxidative stress as well as blocking phosphodiesterase IV, increasing levels of cAMP necessary for memory consolidation.

In some embodiments, the disease or condition associated with oxidative stress and/or inflammation includes, but is not limited to, aging, chronic fatigue syndrome, neurodegenerative disorders, autoimmune disorders, metabolic disorders, and vascular disorders. Neurodegenerative disorders include, for example, Parkinson's disease, Alzheimer's disease, retinal degeneration, hearing loss, fragile X syndrome, traumatic brain injury, spinal cord injury, head injury and demyelinating disorders. Demyelinating disorders include, for example, multiple sclerosis, devic's, progressive multifocal leukoencephalopathy, optic neuritis, leukodystrophies, charcot-marie tooth, and guillian-barre syndrome. Autoimmune disorders include, for example, type I diabetes, rheumatoid arthritis, lupus, colitis and Crohn's disease. Vascular disorders include, for example, stroke, atherosclerosis, myocardial infarction and vascular dementia. Beneficial effects of flavonoids may derive, at least in part, from protection of the cerebral vasculature and microvasculature, such as in stroke, MS, and vascular dementia. Metabolic disorders include, for example, obesity, type II diabetes, and lipid disorders, such as, hypercholesteremia. The compositions described herein may also be useful in the treatment or prevention of certain oxidative stress-mediated orphan disorders, such as amyotrophic lateral sclerosis (ALS), primary progressive MS, charcot-marie-tooth disease, and spinal muscular atrophy. It will be understood that diseases and conditions associated with oxidative stress and/or inflammation may fall into more than one category listed above.

In one embodiment, the disease or condition is a vascular disease, such as stroke.

In some embodiments, the disease or condition is a neurodegenerative disease, such as multiple sclerosis, Parkinson's disease, or Alzheimer's disease.

The composition may be administered in any suitable dosage form. The dosage form may be administered in an amount to deliver an effective amount of the extract or faction thereof. The effective amount may be a therapeutically effective amount, a prophylactically effective amount or an amount for general promotion of good heath.

The dosage requirements vary with the particular formulations and dosage forms employed, the route of administration, the severity of the symptoms presented and the particular subject being treated. Treatment will generally be initiated with small dosages less than the optimum dose of the compound. Thereafter the dosage is increased until the optimum effect under the circumstances is reached. Precise therapeutic dosages may be determined by the administering physician based on experience with the individual subject treated. In general, the active agent is most desirably administered at a concentration that will generally afford effective results without causing harmful or deleterious side effects, and can be administered either as a single unit dose, or if desired, the dosage may be divided into convenient subunits at suitable times throughout the day.

In addition, in vitro or in vivo assays may optionally be employed to help identify optimal dosage ranges. For example, a dose may be formulated in animal models to achieve a beneficial circulating composition concentration range. Initial doses may also be estimated from in vivo data, e.g., animal models, using techniques that are known in the art. Such information may be used to more accurately determine useful doses in humans. One having ordinary skill in the art may optimize administration to humans based on animal data.

The amount of phenolic compounds administered can depend on, among other factors, the subject, the weight of the subject, the health of the subject, the disease being treated, the severity of the affliction, the route of administration, the potency of the active agent, and the judgment of the prescribing physician.

The amount of active agent that will be effective in the treatment of a particular disease, disorder, or condition disclosed herein will depend on the nature of the disease, disorder, or condition, and can be determined by standard clinical techniques known in the art.

In some embodiments, the compositions described herein may be administered in multiple doses. In some embodiments, the compositions described herein may be administered over multiple days, e.g. 2, 3, 4, 5, 7, 10, 15, 20, 30, 40, or more days. The examples provided herein suggest that the protective effects of the compositions may increase over multiple doses (as for example, with antidepressants), thus prolonged or chronic administration may be preferred in some cases. Without being bound by theory, the fact that better results are seen with multiple doses may indicate delayed downstream effects, for example, effects on gene transcription.

In some cases, prolonged administration may be advised in subjects susceptible to one or more of the diseases or conditions recited herein, for example, aging populations or populations with genetic predisposition to certain diseases or conditions (e.g. Parkinson's, Alzheimer's or MS), or subjects having previously experienced a symptom or event associated with one or more of the diseases or conditions recited herein (e.g. stroke).

In some embodiments, the method comprises daily administration of a composition as disclosed herein to a subject. In some embodiments, the method comprises twice daily administration of a composition as disclosed herein to a subject. In some embodiments, the method comprises thrice daily administration of a composition as disclosed herein to a subject.

The administered dose is less than a toxic dose. Toxicity of the compositions described herein may be determined by standard pharmaceutical procedures in cell cultures or experimental animals, e.g., by determining the LD50 (the dose lethal to 50% of the population) or the LD100 (the dose lethal to 100% of the population). The dose ratio between toxic and therapeutic effect is the therapeutic index. In certain embodiments, a pharmaceutical composition may exhibit a high therapeutic index. The data obtained from these cell culture assays and animal studies may be used in formulating a dosage range that is not toxic for use in humans.

Studies have shown that administration of quercetin at doses up to 3000 mg/kg/day for 28 days were well tolerated in mice (Rutz, M. J. et al 2009). In humans, 1 g per day of quercetin for 1 month is safe (Gugler R et al. 1975). Thus, it is likely that high doses of the compositions disclosed herein could similarly be tolerated.

During treatment a dose and dosing schedule may provide sufficient or steady state systemic concentrations of a therapeutically effective amount of flavonoids to prevent or treat a disease or condition. In certain embodiments, an escalating dose may be administered.

The composition may be administered at intervals for as long as necessary to obtain an intended or desired effect.

The phenolic compositions described herein may be used on their own for their health-promoting benefits, or may be used in conjunction with other medicines. In some cases, it may be possible to reduce the amount of the medicine required, thereby having potential to decrease the cost or side effects of treatment.

In another aspect, there is provided a pharmaceutical composition comprising a phenolic composition as described herein together with a pharmaceutically acceptable excipient, such as a carrier or diluent. Typically, in a pharmaceutical application, the composition is administered for treatment or prevention of a disease or condition. In some embodiments, the pharmaceutical composition described herein is for use in the treatment and/or prevention of a disease or condition associated with oxidative stress or inflammation, as described above. The pharmaceutical composition comprises at least one excipient, preferably a pharmaceutical grade excipient, and may be formulated in any suitable dosage form.

The pharmaceutical composition may optionally comprise additional active ingredients, such as a drug.

In some embodiments, the pharmaceutical composition is formulated for enteral administration, topical administration, parenteral administration, or nasal administration. Enteral administration may comprise, for example, oral administration.

Parenteral administration may comprise, for example, intravenous, intrarterial, intracerebral, intraperitoneal, intramuscular, subcutaneous, intracardiac, or intraosseous administration. In some embodiments, the parenteral administration is intravenous administration.

In another aspect, there is provided a use of a composition as described herein in the preparation of a medicament for the treatment and/or prevention of a disease or condition associated with oxidative stress or inflammation.

In another aspect, there is provided a use of a composition as described herein for the treatment and/or prevention of a disease or condition associated with oxidative stress or inflammation.

In some embodiments, the disease or condition associated with oxidative stress or inflammation.

In another aspect, a phenolic composition as described herein is utilized as a food additive (or food ingredient), and may be added various and diverse foods to provide the food item with a significant quantity of phenolics derived from apple skin. While the phenolic composition may be added for its health-promoting benefits, in some embodiments, the phenolic composition may also inhibit or prevent the oxidation of oxidizable compounds, such as polyunsaturated fatty acids (PUFA) and/or lipids, in the food item. The food item may be, for example, a solid, semi-solid (e.g. pudding, yoghurt), or liquid (e.g. beverage) food item. The food item may, for example, be for human or animal consumption.

In another aspect, there is provided a cosmetic product comprising a phenolic composition as described herein. The phenolic composition may be added for its beneficial antioxidant properties and may also inhibit or prevent the oxidation of oxidizable compounds, such as polyunsaturated fatty acids (PUFA) and/or lipids, in the cosmetic composition. The cosmetic product may, for example, be a cream, gel, paste, lotion, emulsion, ointment, or a microencapsulated product.

In another embodiment, there is provided a functional food or beverage comprising a fraction as disclosed herein.

In other aspects, there are provided commercial packages comprising compositions as described herein together with instructions for use.

Any suitable apple cultivar may be used in accordance with the present disclosure.

In some embodiments, the apple is a dessert and dual purpose apple, such as, Adams Pearmain, Alkmene, Ambrosia, Antonovka, Arlet, Ariane, Arkansas Black, Ashmead's Kernel, Aurora Golden Gala, Baldwin, Ben Davis, Blenheim Orange, Beauty of Bath, Belle de Boskoop, Bohemia, Braeburn, Brina, Cameo, Clivia, Cornish Gilliflower, Cortland, Cox's Orange Pippin, Cripps Pink (Pink Lady), Delbarestivale® delcorf, Delbardivine® delfloga, Discovery, Ecolette, Egremont Russet, Elstar, Empire, Esopus Spitzenburg, Fuji, Gala, Ginger Gold, Golden Orange, Golden Delicious, Granny Smith, Gravenstein, Grimes Golden, Haralson, Honeycrisp, Idared, James Grieve, Jazz, Jersey Black, Jonagold, Jonathan, Junaluska, Karmijn de Sonnaville, Knobbed Russet, Liberty, Macoun, McIntosh, Mutsu, Newtown Pippin, Nickajack, Nicola, Novaspy, Novamac, Paula Red, Pink Pearl, Pinova, Rajka, Ralls Genet, Rambo, Red Delicious, Rhode Island Greening, Ribston Pippin, Rome, Royal Gala, Roxbury Russet, Rubens (Civni), Santana, Saturn, Sekai Ichi, Spartan, Stayman, Sturmer Pippin, Summerfree, Taliaferro, Topaz, Worcester Pearmain, York Imperial or Zestar.

In some embodiments, the apple is a cooking apple, for example, selected from Bramley, Calville Blanc d'hiver, Chelmsford Wonder, Flower of Kent, Golden Noble, Norfolk Biffin or Northern Spy.

In some embodiments, the apple is a cider apple, for example, selected from Brown Snout, Dabinett, Foxwhelp, Harrison Cider Apple, Kingston Black, Redstreak or Styre.

In some embodiments, the apple is a crabapple.

In some embodiments, the apple is Northern Spy.

The following non-limiting examples are provided to illustrate, and assist the reader in understanding, the present disclosure.

EXAMPLES

Example 1

Preparation of Flavonoid-Rich Fractions of Apple Skin Extract

The apple skins of the apple cultivar, Northern Spy, were collected from a commercial pie manufacturer, Apple Valley Foods Inc., Kentville, NS, Canada. Immediately after peeling, the skins were treated with 2% $CaCl_2$ in water (w/v) at 55±5° C. for 10 min to prevent degradation of phenolic compounds. After draining the excess water and within 3 h of the $CaCl_2$ treatment, the apple skins were transported in plastic containers to the Nova Scotia Agricultural College (NSAC). The apple skins were dried in clean plastic trays at 60±2° C. for 48 h using a convection oven with air circulation (Milner Agincourt, ON, Canada). The dried skins were ground into a fine powder using a Willey mill with 1 mm sieve screen (Model Laboratory Heavy Duty, Arthur Thomas Co., Philadelphia, Pa.) and kept in a freezer (−80° C.) for later use. One hundred grams of apple skin powder was weighed into a 2 L flask and sonicated using 1 L of absolute ethanol two times for 15 min with 10 min interval. The suspension was then transferred into 50 mL corning tubes for centrifugation at 3000 rpm for 15 min. The supernatants of two of the above extractions (total of 200 g of apple skins in 2 L of ethanol) were collected and evaporated to produce 200 mL concentrate using a rotary evaporation system at 45° C. (Rotavap® R-200, Buchi, Flawil, Switzerland).

For the fractionation of the above concentrated apple skin extract, flash chromatography using a polymeric sorbent (Sorbent SP207-05 Sepabeads resin brominated styrenic adsorbent; particle size 250 μm, surface area 630 $m^2/g$) was used. The chromatography column (3.8×45 cm, Sati International Scientific Inc., Dorval, QC, Canada) containing the 600 g adsorbent was conditioned with deionized water and loaded with apple skin extract at the top of the column. The column was immediately washed with water by sending 2 to 3 times of bed volume of water through it. The removal of sugar from the crude extract was monitored by measuring the Brix value of wash water using a refractometer. Once the Brix value was less than 1%, washing step was terminated. The phenolic compounds retained in the column were eluted using a step gradient of ethanol (Table 1, 800 mL of each elusion) and the elute was concentrated to 20 mL using a rotary evaporator (Rotavap® R-200, Buchi, Flawil, Switzerland) at 45° C.

TABLE 1

The percentage of ethanol used for the step-gradient of elusions of phenolic compounds using the C-18 column.

| Fraction Number | Percent ethanol |
|---|---|
| F1 | 20% |
| F2 | 30% |
| F3 | 40% |

TABLE 1-continued

The percentage of ethanol used for the step-gradient of elusions of phenolic compounds using the C-18 column.

| Fraction Number | Percent ethanol |
|---|---|
| F4 | 45% |
| F5 | 50% |
| F6 | 55% |
| F7 | 60% |
| F8 | 65% |
| F9 | 70% |
| F10 | 75% |
| F11 | 80% |
| F12 | 90% |
| F13 | 100% |
| F14 | 100% |
| F15 | 100% |

LC-MS/MS Analysis of Phenolics in the C-18 Fractions.

Analyses of major individual phenolic compounds present in 15 apple peel fractions (Tables 2a and 2b) were performed according to the procedure reported by Rupasinghe et al. (2010). The apple peel fractions are numbered F1 through F15.

All analyses were performed using a Waters Alliance 2695 separations module (Waters, Milford, Mass.) coupled with a Micromass Quattro micro API MS/MS system and controlled with Masslynx V4.0 data analysis system (Micromass, Cary, N.C.). The column used was a Phenomenex Luna $C_{18}$ (150 mm×2.1 mm, 5 µm) with a Waters X-Terra MS $C_{18}$ guard column. For the separation of the flavonol, flavan-3-ol, phenolic acid and dihydrochalcone compounds, a gradient elution was carried out with 0.1% formic acid in water (solvent A) and 0.1% formic acid in acetonitrile (solvent B) at a flow rate of 0.35 mL/min. A linear gradient profile was used with the following proportions of solvent A applied at time t (min); (t, A %): (0, 94%), (9, 83.5%), (11.5, 83%), (14, 82.5%), (16, 82.5%), (18, 81.5%), (21, 80%), (29, 0%), (31, 94%), (40, 94%). The analysis of cyanidin-3-O-galactoside was carried out using the mobile phases of 5% formic acid in water (solvent A) and 5% formic acid in methanol (solvent B) at a flow rate of 0.35 mL/min. The linear gradient profile used was as follows; (t, A %): (0, 90%), (10, 70%), (17, 60%), (21, 48.8%), (26, 36%), (30, 10%), (31, 90%), (37, 90%).

Electrospray ionization in negative ion mode (ESI−) was used for the analysis of the flavonol, flavan-3-ol, phenolic acid and dihydrochalcone compounds. The following conditions were used: capillary voltage −3000 V, nebulizer gas ($N_2$) temperature 375° C. at a flow rate of 0.35 mL/min. For the analysis of cyanidin-3-O-galactoside, electrospray ionization in positive ion mode (ESI+) was used. The settings for the positive ion experiments were as follows: capillary voltage 3500 V, nebulizer gas 375° C. at a flow rate of 0.35 mL/min. The cone voltage (25 to 50 V) was optimized for each individual compound. Multiple reaction-monitoring (MRM) mode using specific precursor/product ion transitions was employed for quantification in comparison with standards: m/z 301→105 for Quercetin (Q), m/z 609→301 for Q-3-O-rutinoside, m/z 463→301 for Q-3-O-glucoside and Q-3-O-galactoside, m/z 448→301 for Q-3-O-rhamnoside, m/z 595→301 for Q-3-O-peltoside, m/z 273→167 for phloritin, m/z 435→273 for phloridzin, m/z 353→191 for chlorogenic acid, m/z 179→135 for cafeic acid, m/z 193→134 for ferulic acid and isoferulic acid, m/z 449→287 for cyanidin-3-O-galactoside, m/z 289→109 for catechin, m/z 290→109 for epicatechin, and m/z 305→125 for epigalocatechin. In MRM experiments, both quadrupoles were operated at unit resolution.

TABLE 2a

Concentration (mg/L) of phenolic compounds in Fractions 1 to 7.

| Phenolic compound | F1 | F2 | F3 | F4 | F5 | F6 | F7 |
|---|---|---|---|---|---|---|---|
| Quercetin (Q) | 0.1 | 0.1 | 0.6 | 9.9 | 20.6 | 11.9 | 50.2 |
| Q-3-O-paltoside | 0 | 0 | 7.2 | 63.8 | 29.0 | 2.3 | 0 |
| Q-3-O-rutinoside | 0 | 0 | 293.3 | 1535.7 | 1105.0 | 285.1 | 30.3 |
| Q-3-O-galactoside | 2.0 | 1.2 | 566.8 | 2914.9 | 3914.7 | 2346.1 | 575.8 |
| Q-3-O-glucoside | 0.5 | 0.3 | 101.6 | 1474.8 | 1657.1 | 721.5 | 101.7 |
| Q-3-O-rhamnoside | 1.8 | 1.0 | 86.9 | 2771.6 | 4339.2 | 3112.8 | 973.6 |
| Total Flavonols | 4.4 | 2.6 | 1056.40 | 8770.7 | 11065.6 | 6479.7 | 1731.6 |
|  | (48.4%) | (1.6%) | (23.1%) | (72.3%) | (84.2%) | (86.9%) | (85.7%) |
| Cyanidin-3-O-galactoside | 0 | 0 | 527.6 | 559.4 | 167.4 | 29.2 | 6.3 |
|  | (0%) | (0%) | (11.5%) | (4.6%) | (1.2%) | (0.3%) | (0.3%) |
| Phloridzin | 1.3 | 0.9 | 7.7 | 386.8 | 711.5 | 614.1 | 239.9 |
| Phloritin | 0.8 | 0 | 0.8 | 1.0 | 1.2 | 1.2 | 1.8 |
| Total dihydrochalcone | 2.1 | 0.9 | 8.5 | 387.8 | 712.7 | 615.3 | 241.7 |
|  | (23.1%) | (0.56%) | (0.1%) | (3.1%) | (5.4%) | (8.2%) | (11.9%) |
| Chlorogenic acid | 1.9 | 99.8 | 1663.0 | 1221.1 | 502.8 | 97.7 | 10.4 |
| Cafeic acid | 0.7 | 0.9 | 2.1 | 43.6 | 25.1 | 7.0 | 1.4 |
| Ferulic acid | 0 | 0 | 1.2 | 0 | 13.3 | 20.3 | 5.8 |
| Isoferulic acid | 0 | 0 | 0 | 3.7 | 23.5 | 13.9 | 4.3 |
| Total phenolic acids | 2.6 | 100.7 | 1666.3 | 1268.4 | 564.7 | 138.9 | 21.9 |
|  | (28.6%) | (62.8%) | (36.4%) | (10.4%) | (4.3%) | (1.9%) | (1.1%) |
| Epigallocatechin | 0 | 0.9 | 7.4 | 0.9 | 2.9 | 1.3 | 0 |
| Catechin | 0 | 15.7 | 210.4 | 106.8 | 46.0 | 13.2 | 1.7 |
| Epicatechin | 0 | 39.4 | 1104.8 | 1044.3 | 579.3 | 178.2 | 16.8 |
| Total Flavan-3-ol | 0 | 56.0 | 1322.6 | 1152.0 | 628.2 | 192.7 | 18.5 |
|  | (0%) | (34.9%) | (28.9%) | (9.5%) | (4.8%) | (2.6%) | (0.9%) |
| Total phenolics | 9.1 | 160.2 | 4578.4 | 12138.3 | 13138.6 | 7455.8 | 2020 |

TABLE 2b

Concentration (mg/L) of phenolic compounds in Fractions 8 to 15.

| Phenolic compound | F8 | F9 | F10 | F11 | F12 | F13 | F14 | F15 |
|---|---|---|---|---|---|---|---|---|
| Quercetin (Q) | 45.0 | 53.8 | 68.2 | 1.4 | 32.1 | 10.7 | 7.7 | 0.5 |
| Q-3-O-paltoside | 0 | 0 | 0 | 0 | 0 | 0 | 0 | 0 |
| Q-3-O-rutinoside | 4.9 | 1.5 | 0 | 0 | 0 | 0 | 2.4 | 0 |
| Q-3-O-galactoside | 75.8 | 21.7 | 11.7 | 6.8 | 5.5 | 7.5 | 33.4 | 10.6 |
| Q-3-O-glucoside | 14.2 | 3.7 | 2.4 | 1.2 | 1.2 | 1.2 | 5.4 | 2.1 |
| Q-3-O-rhamnoside | 176.4 | 34.3 | 11.9 | 5.7 | 3.9 | 3.2 | 19.4 | 19.5 |
| Total Flavonols | 316.3 (82.4%) | 115 (84.4%) | 94.2 (89.6%) | 15.1 (70.6%) | 42.7 (65.8%) | 22.6 (45.9%) | 68.3 (77.4%) | 32.7 (74.7%) |
| Cyanidin-3-O-galactoside | 1.9 (0.4%) | 1.1 (0.8%) | 0.8 (0.7%) | 0.5 (2.3%) | 0.6 (0.9%) | 0.6 (1.2%) | 0.7 (0.8%) | 0.5 (1.1%) |
| Phloridzin | 53.6 | 12.0 | 4.3 | 2.6 | 2.2 | 1.7 | 6.5 | 7.9 |
| Phloritin | 3.1 | 3.3 | 1.8 | 1.0 | 0.1 | 0.9 | 0.9 | 0.8 |
| Total dihydrochalcone | 56.7 (14.7%) | 15.3 (11.2%) | 6.1 (5.8%) | 3.6 (16.8%) | 3.2 (4.9%) | 2.6 (5.3%) | 7.4 (8.4%) | 8.7 (19.9%) |
| Chlorogenic acid | 3.3 | 2.3 | 2.0 | 1.7 | 10.5 | 9.5 | 4.2 | 1.2 |
| Cafeic acid | 0.8 | 0 | 0.7 | 0 | 0.8 | 0.8 | 0.8 | 0.7 |
| Ferulic acid | 1.7 | 1.1 | 0 | 0 | 0 | 0 | 0 | 0 |
| Isoferulic acid | 0.9 | 0 | 0 | 0 | 0 | 0 | 0 | 0 |
| Total phenolic acids | 6.7 (1.7%) | 3.4 (2.5%) | 2.7 (2.6%) | 1.7 (7.9%) | 11.3 (17.4%) | 10.3 (20.9%) | 5.0 (5.7%) | 1.9 (4.3%) |
| Epigallocatechin | 0 | 0 | 0 | 0 | 0 | 0 | 0 | 0 |
| Catechin | 0 | 0 | 0 | 0 | 1.9 | 1.8 | 0.9 | 0 |
| Epicatechin | 2.3 | 1.5 | 1.3 | 0.5 | 5.2 | 11.3 | 5.9 | 0 |
| Total Flavan-3-ol | 2.3 (0.6%) | 1.5 (1.1%) | 1.3 (1.2%) | 0.5 (2.3%) | 7.1 (10.9%) | 13.1 (26.6%) | 6.8 (7.7%) | 0 |
| Total phenolics | 383.9 | 136.3 | 105.1 | 21.4 | 64.9 | 49.2 | 88.2 | 43.8 |

In Tables 2a and 2b, the values shown in brackets represent the percentage of that component relative to the total phenolic content measured in that fraction, where the total phelolic amount shown at the bottom of each row represents 100% for that fraction. It can be seen that different fractions may have different phenolic profiles based on the relative amounts of each component in the fraction. The various fractions may further contain additional unidentified components.

It was determined that Fractions F4 and F5 had the highest concentration of phenolic compounds, with F4 having 12138.3 mg/L, and F5 having 13138.6 mg/L total phenolics concentration per 800 ml eluted fraction.

When looking at the amount of a particular component (e.g. total phenolic content) across horizontal rows in Tables 2a and 2b, the relative amount of that component compared to the crude extract can be roughly estimated. For example, F4 and F5 contain approximately 30% and 32.5%, respectively, of the total phenolic content of the 15 fractions. Fractions F4 and F5 also had the highest flavonol content. Without wishing to be bound by theory, it is believed that these fractions are particularly effective due to the high flavonol content of these fractions. It is also possible that there are synergies between the components in the fractions.

Example 2

Neuroprotective Effects of F5 in an Animal Model of Stroke

F5 Treatment

The neuroprotective potential of phenolic composition F5 (Table 2a) derived from apple peel was investigated in an hypoxia-ischemia (HI) model of brain injury. The total phenolic content of the fraction was measured, based on the phenolic compounds listed in Table 2a. The extract was administered to C57/b16 mice (6-8 weeks old) by oral gavage for 3 consecutive days at a dose of 50 mg phenolics/kg body weight. Mice in a control group were given vehicle (water) at a volume of 0.01 ml/g body weight by oral gavage for 3 consecutive days. Twenty-four hours after the last dose of extract or vehicle, the mice were subjected to hypoxia-ischemia (HI).

A separate study had shown that a single dose (50 mg phenolics/kg) was not sufficient to significantly protect against damage caused by hypoxia-ischemia compared to vehicle treatment group (data not shown), suggesting that increased dosage or multiple treatments are required.

Brain Injury Induced by Hypoxia-Ischemia (HI)

The hypoxia-ischemia (HI) method originally reported by Levine (1960) for rats was used to induce cerebral ischemia. The procedure was slightly modified to accommodate the use of adult mice. Mice were anaesthetised using Isoflurane in an induction chamber (3% vaporised with medical oxygen at a rate flow of 3 L/min). Anaesthesia was maintained with 2% Isoflurane vaporised with oxygen flowing at a rate of 1.5 L/min. A small midline incision was made on the ventral neck with scissors and the underlying tissue was bluntly dissected until the sternohyoid and sternomastoid muscles were exposed. The left common carotid artery was located just below the region where the sternohyoid and sternomastoid meet. The vagus nerve was carefully separated from the carotid artery. The left carotid artery was permanently occluded with a high-temp elecrocautery pen. Animals in which the common carotid artery was not completely sealed or exhibited blood loss were immediately euthanized. After a recovery period of 2-3 hrs the mice were placed in a glass cylinder vented with 8% oxygen balanced nitrogen flowing at a rate of 6 L/min. The glass cylinder was placed in a water bath at 36.5° C. to maintain body temperature. After 50 min exposure to the low oxygen environment (8%) the mice were removed from the chamber and returned to their cage. Mice were allowed to survive for 2 weeks following HI to permit the brain infarct in the ipsilateral hemisphere to develop before harvesting brain tissue for histological analysis.

Rotarod

The rotarod is a behavioral test that assesses motor performance in rodents. The apparatus consists of a rotating cylinder that mice walk along. The rotational speed increases at a constant acceleration making it more difficult for mice to continue walking. The amount of time spent on the rod (latency period for the animal to fall off the rod) was recorded as a measure of performance, with longer times indicative of better motor performance. The acceleration of the rotarod was set to 100 rot/min$^2$. Mice were tested on the third day of F5 treatment (24 hrs pre-HI) and 2 weeks following HI (14 days post-HI). On each of these days the mice were tested with 3 sessions and the average time spent on the rotarod was calculated for that day. The difference in performance 14 days post-HI and 24 hrs pre-HI was determined and compared between the two treatment groups.

Preparation of Tissue for Histology

Two weeks following HI the mice were humanely killed by an IP injection of sodium pentobarbital at a dose of 240 mg/kg. The mice were transcardially perfused with 0.9% saline then 4% paraformaldehyde (PFA) in phosphate buffer at a pH of 7.4. Post-fixation was achieved by storing the brains for 48-72 hrs in 4% PFA. The tissue was cryoprotected by submerging in a solution of 30% sucrose in 0.1 M phosphate buffer for 24 hrs. Free floating coronal sections were cut on a freezing microtome at a thickness of 30 µm and placed in a solution of phosphate buffered saline (PBS) with 5% sodium azide for long-term storage.

Nissl Staining

Sections 360 µm apart were mounted onto superforst glass slides and dried overnight. Serial brain sections about 30 µm thick were cut from the anterior and mid portion of the dorsal hippocampus. The sections were dehydrated using a graded ethanol series of increasing strength (2 min of 50%, 70%, 95%, 100%) then incubated in xylenes for 5 min followed by rehydration using another graded series of ethanol of increasing dilution (100%, 95%, 70%, 50%). Brain sections were then rinsed in water and incubated in a 1% cresyl violet solution for 10-15 min. The sections were rinsed and destained in a 1% acetic acid before being dehydrated through a graded series of ethanol solutions of increasing strength (50%, 70%, 95%, 100%). The tissue was cleared in xylenes then coverslipped using Cytoseal. Images of the sections were captured using PixeLink software with a 1× lens and a 10× objective. The images were analyzed using ImageJ software. The area of the hemisphere ipsilateral to common carotid artery occlusion and the area of the contralateral hemisphere were measured for all sections and a ratio of ipsilateral/contralateral area was calculated to determine hemisphere loss. A ratio of 1.0 indicated no hemisphere loss, while ratios less than 1.0 indicated loss.

Neuronal Nuclei (NeuN) Immunohistochemistry

To prepare tissue for immunohistochemical staining the brain sections were rinsed three times with PBS containing 0.1% Triton X (PBS-TX) for ten minutes at room temperature (same for all subsequent washes). The sections were then placed in PBS-TX containing 1% hydrogen peroxide for 30 minutes to quench endogenous peroxidases. The tissue was again washed before being incubated in 5% horse serum in PBS-TX. Following incubation in serum the tissue was incubated with primary antibody at room temperature for one hour then shaken at 4° C. overnight. The primary antibody was a monoclonal anti-NeuN antibody raised in mouse used at a 1:2000 dilution in PBS-TX. After incubation overnight in primary antibody, the tissue was washed and incubated for one hour in the secondary antibody, anti-mouse raised in horse, used at a dilution of 1:500. Another series of washes was performed and the tissue was incubated in an Avidin-Biotin complex in PBS-TX at a dilution of 1:1000 for one hour to amplify the signal of the secondary antibody. The sections were washed and then placed in a solution of 0.5 mg/ml diaminobenzidine (DAB) with nickel, glucose oxidase, D-glucose, and ammonium chloride in PBS. The tissue was reacted with the DAB solution for 5-10 minutes until staining of desired density was achieved. The tissue was then washed in PBS, mounted on superfrost glass slides and left overnight to dry. The sections were then dehydrated in a graded ethanol series (50%, 70%, 95%, and 100%), cleared in Xylene, and coverslipped using Cytoseal. Sections stained for NeuN immunoreactivity in the striatum at 0.1 mm anterior to bregma and the hippocampus at 1.8 mm posterior to bregma were captured on a light microscope using PixeLink software at 50× (10× objective and a 5× lens). The images were then analyzed using ImageJ software by an observer blind to the treatment group. Cell counts in the striatum were obtained by first converting the image to an 8-bit grey scale. The binary tool was selected so that only pixels above a threshold of 3× background were black on a white foreground. The striatum was outlined and the positively labelled cells were counted using the analyze particles function. An index of neuronal survival was calculated by dividing the number of NeuN positive cells in the ipsilateral striatum by the number of NeuN positive cells in the contralateral striatum to yield a cell survival ratio. A value of 1.0 indicated no injury in the ipsilateral striatum while a value of less than 1.0 indicated neuronal loss. The images of the hippocampus were converted to 8-bit grey scale and the binary tool was selected so that only positively labelled cells were black on a white foreground. The hippocampus was outlined and the area of labelled cells was measured with the measurement function. In the case of the dorsal hippocampus, the dense packing of pyramidal neurons precluded cell counts in sections 30 µm thick. Neuronal loss was therefore estimated by measuring the area occupied by NeuN positive cells in the entire hippocampus of sections cut at 1.8 mm posterior to bregma. The area occupied by NeuN positive neurons in the ipsilateral hippocampus was divided by the area occupied by NeuN positive neurons in the contralateral hippocampus to obtain an index of neuronal loss for this structure. An index of 1.0 indicated no neuronal loss in the ipsilateral hippocampus, while values less than 1.0 indicated neuronal loss.

Results

In reference to FIG. 1, it can be seen that mice treated with F5 had better motor performance as assessed by the rotarod compared to mice treated with vehicle.

Motor performance was assessed in the mice before and after HI as a measure of neurological capacity. The difference in rotarod performance (14 days post-HI—24 hrs pre-HI) was greater for the group that was treated with F5 than the control mice that received water. On average, mice in the F5 group improved their score following HI with a mean±standard error of the mean (SEM) difference of 3.7±2.5 seconds (s). Mice treated with vehicle performed worse following HI with a mean±SEM difference of −5.7±2.7 s. A two-sided student's t-test determined a significant difference between these 2 group (t (45)=2.53; P=0.015). F5 treatment therefore improved the neurological outcome following HI compared to vehicle treatment.

Figure 2:
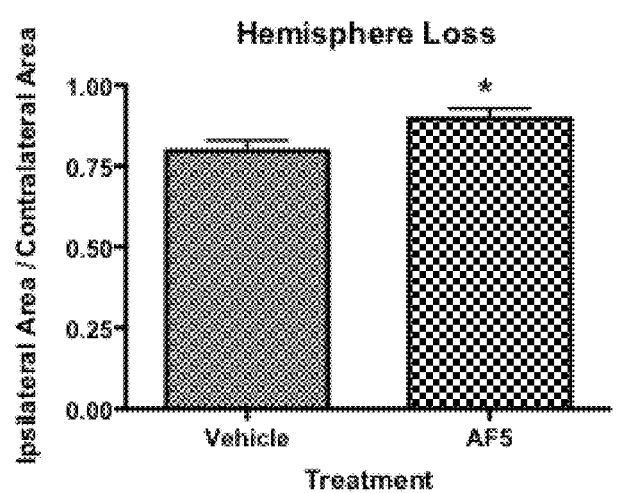
FIG. 2 illustrates that mice treated with F5 were protected from the hemisphere loss caused HI brain injury compared to vehicle treated mice.

In reference to FIG. 2, it can be seen that mice treated with F5 (50 mg/kg/day for 3 days) were protected from the hemisphere loss caused by HI compared to vehicle treated mice.

As a result of the injurious effects of HI the brain hemisphere on the side ipsilateral to internal carotid cauterization becomes damaged and may experience tissue loss.

The mice treated with F5 experienced smaller hemisphere loss following HI with a mean±SEM ipsilateral/contralateral ratio of 0.90±0.03 while mice treated with vehicle had a mean±SEM ratio of 0.80±0.03. The difference between groups was found to be statistically significant using a two-sided student's t-test (t(45)=2.12; P=0.040). The apple fraction F5 was therefore protective against the infarction caused by HI.

Figure 3:
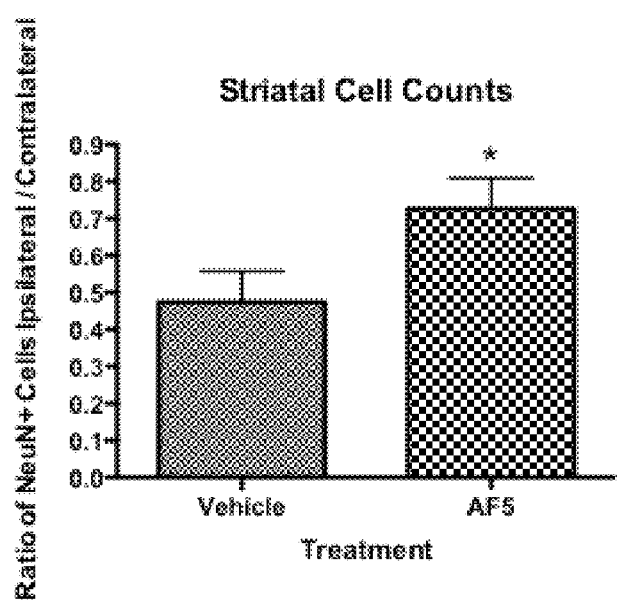
FIG. 3 illustrates that F5 treatment increased the number of viable neurons in the striatum after HI brain injury compared to vehicle treatment.

In reference to FIG. 3, it can be seen that F5 treatment increased the number of viable neurons in the striatum after HI compared to vehicle treatment.

Cell death following HI occurs in several brain regions following HI. One region that is sensitive to neuronal death following HI is the striatum. To assess neuronal loss following HI, brain sections were stained with the immunohistochemical marker NeuN to demark viable neurons. The number of neurons was counted in both the ipsilateral and contralateral striata at 1.0 mm anterior to bregma. The ipsilateral/contralateral ratio was calculated to assess neuronal loss. It was found that mice given the F5 extract experienced a mean count±SEM of 0.73±0.08, while the mice treated with vehicle had a mean of 0.47±0.08. The difference between the two groups was found to be statistically significant using the two-sided student's t-test (t(45)=2.126; P=0.039). Therefore the apple extract was found to increase the number of viable neurons in the striatum following HI compared to the vehicle treated group.

Figure 4:
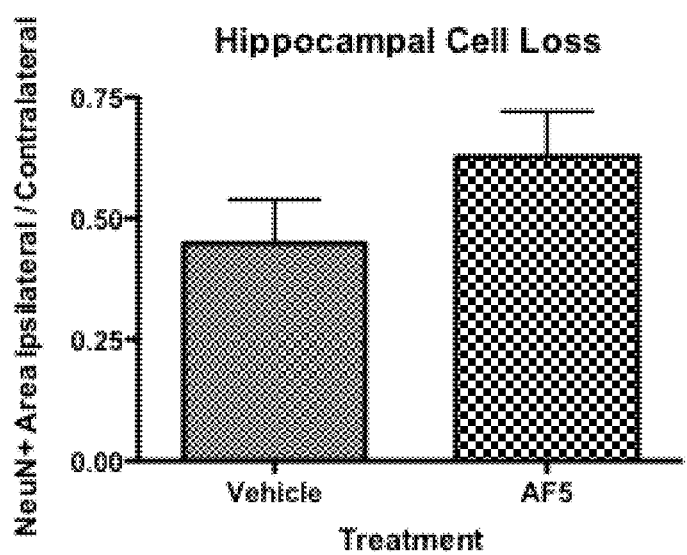
FIG. 4 illustrates that a single F5 treatment did not significantly prevent cell loss in the hippocampus after HI brain injury in comparison to the vehicle control group.

Another brain region where neuronal death occurs is the hippocampus. To assess the cell loss in the hippocampus following HI the brain sections were stained immunohistochemically with NeuN. The area of NeuN positive neurons was measured in both the ipsilateral and contralateral hippocampus at 1.8 mm anterior to bregma. A ratio was determined by dividing the area of NeuN positive staining in the ipsilateral hippocampus divided by the area of staining in the contralateral hemisphere. In reference to FIG. 4, it can be seen that F5 treatment did not significant prevent cell loss in the hippocampus in comparison to the vehicle control group. The mice treated with F5 had a mean±SEM ratio of 0.63±0.09, while the vehicle control group showed a mean±SEM of 0.45±0.09. The difference between the two groups was not found to be significant, with a P value of 0.1771 (determined by a two sided student's t-test). The results suggest that F5 treatment was not protective in the hippocampus under the parameters tested. Further studies will explore whether different dosages or treatment regimes may extend protection to the hippocampus region.

The results to date suggest that 3 doses of F5 prior to HI is neuroprotective against tissue loss, as well as in protecting against the motor performance deficits experienced by those mice in the vehicle treatment group following HI.

Figure 5:
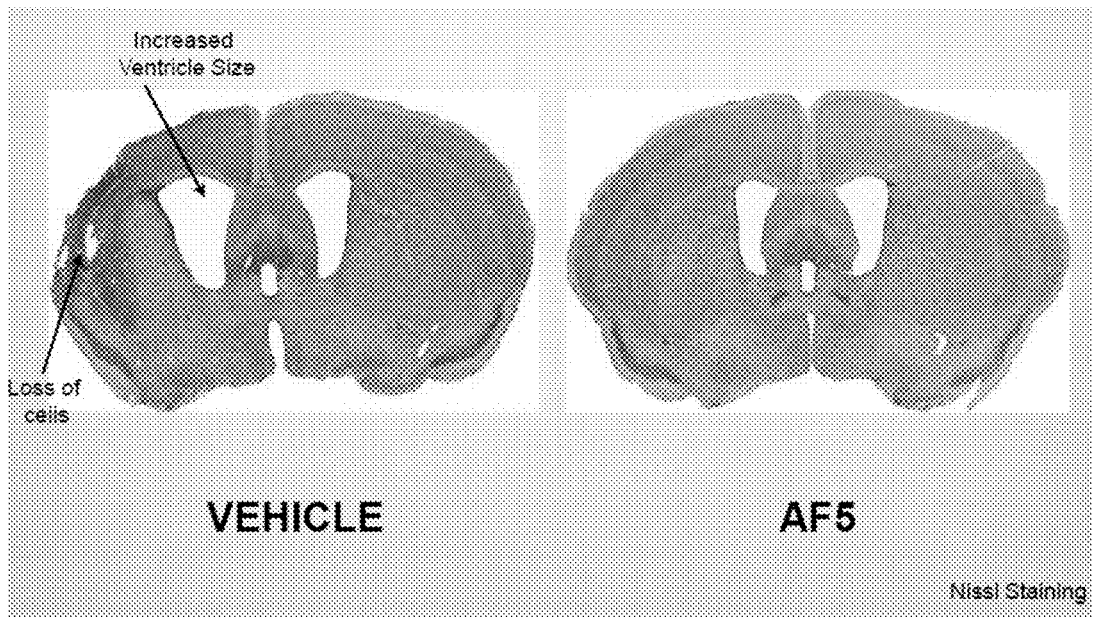
FIG. 5 is a photomicrograph showing brain volume in vehicle (water)- and F5-treated mice and after HI brain injury.
Figure 6:
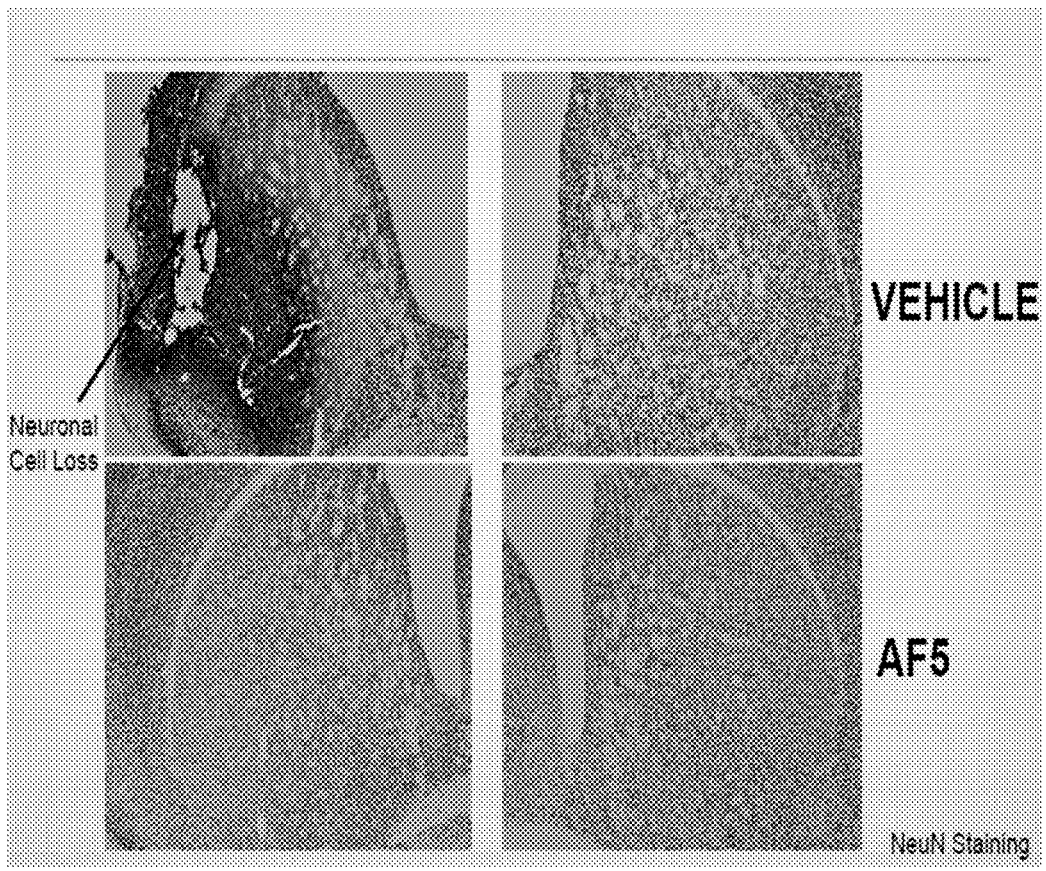
FIG. 6 is a photomicrograph showing striatal damage in vehicle (water)- and F5-treated mice after HI brain injury.

Representative Photos are shown in FIGS. 5 and 6. Images selected were the animal with the median score for respective group.

Example 3

F4 Reduces Death of Primary Cortical Neurons Subjected to Oxygen Glucose Deprivation when Compared to Two F4 Components and Three F4 Metabolites Methods Lactate dehydrogenase is a stable cytosolic enzyme that is released by necrotic cells upon membrane damage. The membrane integrity of cortical neurons was assayed by measuring the release of lactate dehydrogenase (LDH) using the Cytotoxicity Detection Kit$^{PLUS}$ (Roche Applied Science). This assay kit detects LDH released into culture supernates by a coupled enzymatic reaction. Positive (100% LDH release) and negative (spontaneous LDH release) controls were prepared in triplicate according to the manufacturer's instructions. Primary cortical neuron cultures were prepared from cerebral cortices of embryonic day 16 CD1 mouse embryos. Cortical neuron cultures were exposed to vehicle (0.1% dimethyl sulfoxide (DMSO)) or F4 at concentrations of 1, 0.1 or 0.01 µg/mL in serum-free conditions for a period of 12 h before they were subjected to oxygen glucose deprivation (OGD). The neurons were exposed to vehicle or F4 at concentrations of 1, 0.1 or 0.01 µg/mL phenolics throughout the 12 h period of OGD. Following, cell culture supernates were collected for determination of released LDH. Absorbance was measured at 490 nm with a reference wavelength of 620 nm. Percentage of total LDH release was calculated by following the instructions provided by the manufacturer. Background was subtracted and LDH release in each sample was expressed as a percentage of the positive control.

Figure 7:
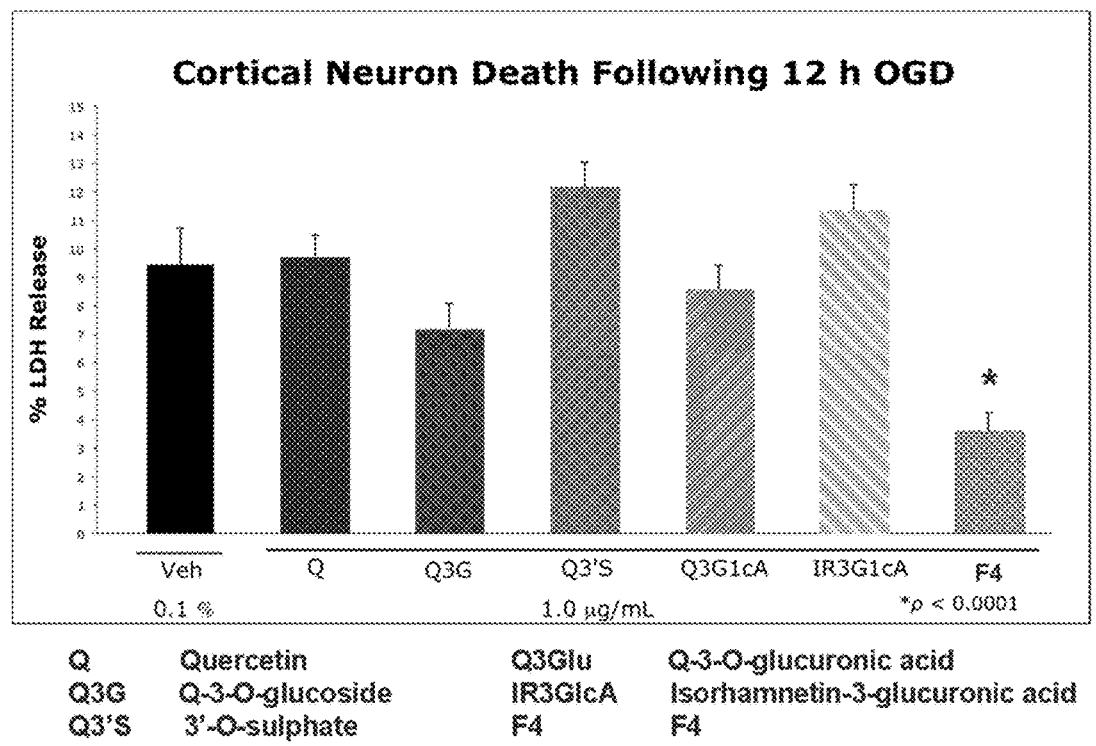
FIG. 7 illustrates that F4 reduced the death of primary cortical neurons subjected to oxygen glucose deprivation in a comparison of F4, F4 components and F4 metabolites.

In reference to FIG. 7, it can be seen that F4 significantly reduces the death of primary cortical neurons subjected to oxygen glucose deprivation whereas no significant reduction was seen when cells were treated with two active components of F4 (Q and Q3G) or three metabolites (Q3'S, Q3Glu, IR3GlcA). Primary cortical cultures that were exposed to 1 µg/mL of F4 were significantly protected from necrotic cell death induced by OGD (p<0.0001), as compared with vehicle-treated cells. F4 had a direct neuroprotective effect on cortical neurons under oxidative stress.

The results demonstrate that F4 is able to reduce neuronal cell loss in an experimental model of stroke (hypoxic-ischemic brain injury) at least in part by directly protecting neurons from the damaging effects of ischemia (no glucose, no oxygen).

Example 4

F4 is Protective Against Hypoxic-Ischemic (HI) Brain Damage In Vivo

The Methods for hypoxic-ischemic (HI) brain injury; NeuN staining, an image analysis are the same described in the examples above.

Figure 8:
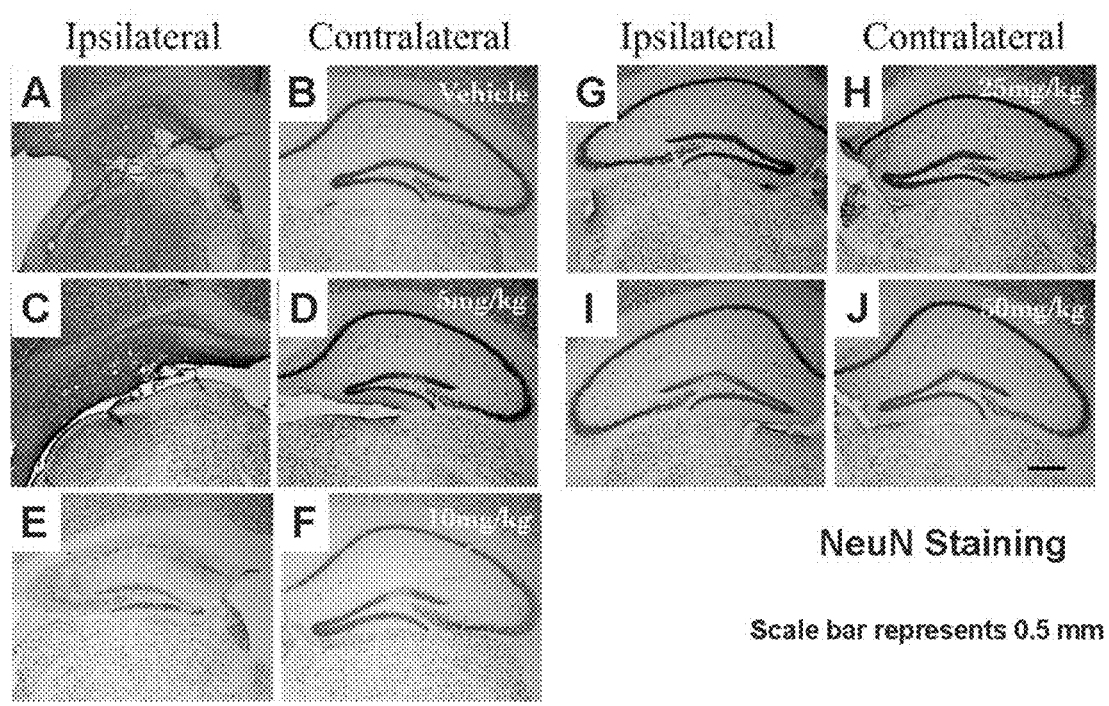
FIG. 8 illustrates a dose-dependent reduction in HI-induced hippocampal neuron loss produced by oral (p.o.) administration of F4.
Figure 9:
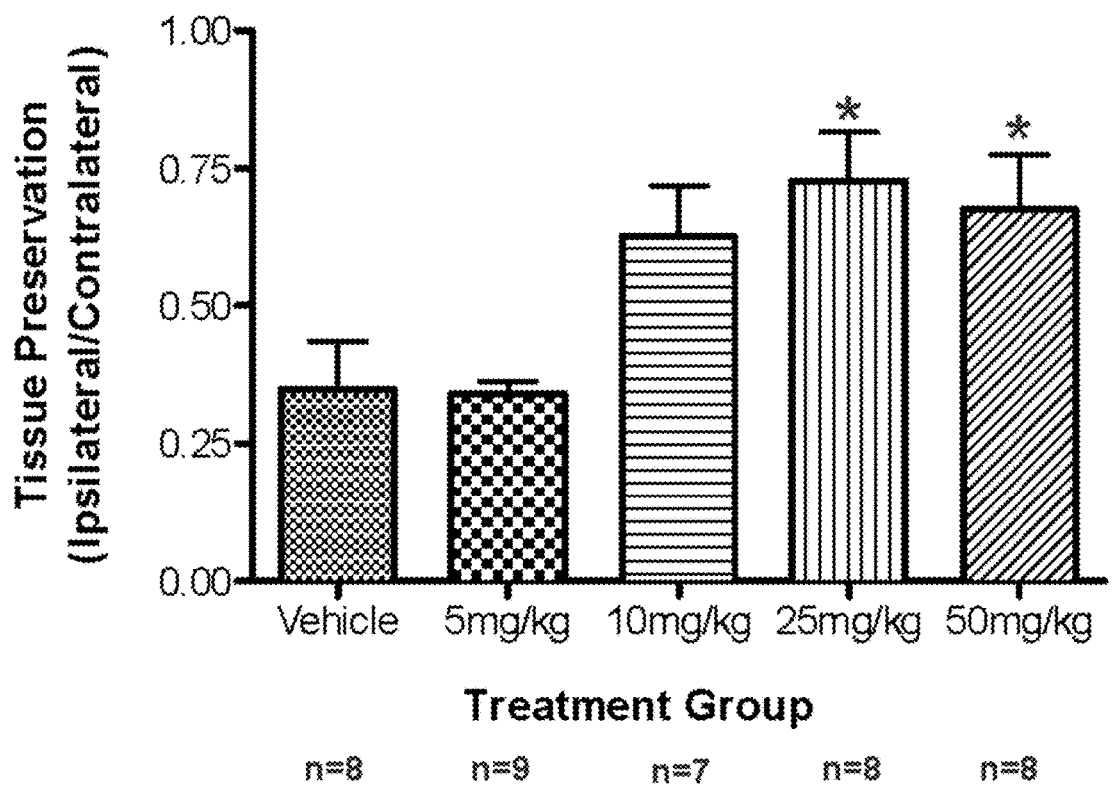
FIG. 9 illustrates a dose-dependent reduction of HI-induced hippocampal damage by a purified apple fraction F4.
Figure 10:
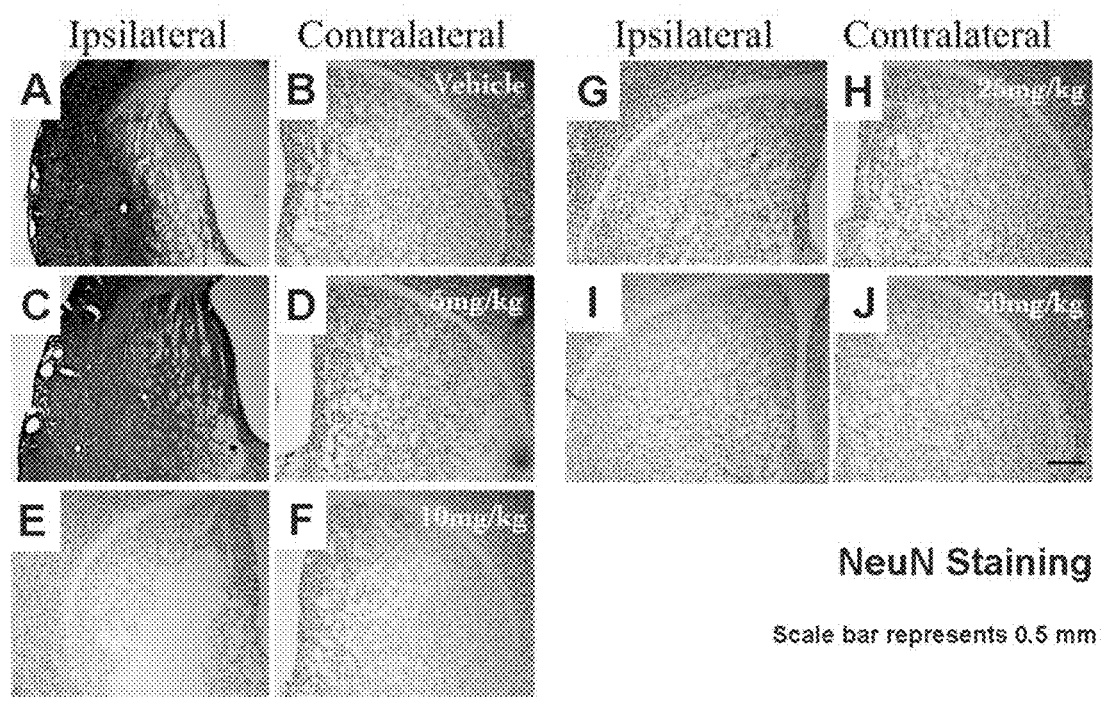
FIG. 10 illustrates a dose-dependent reduction of HI-induced striatal neuron loss produced by F4.
Figure 11:
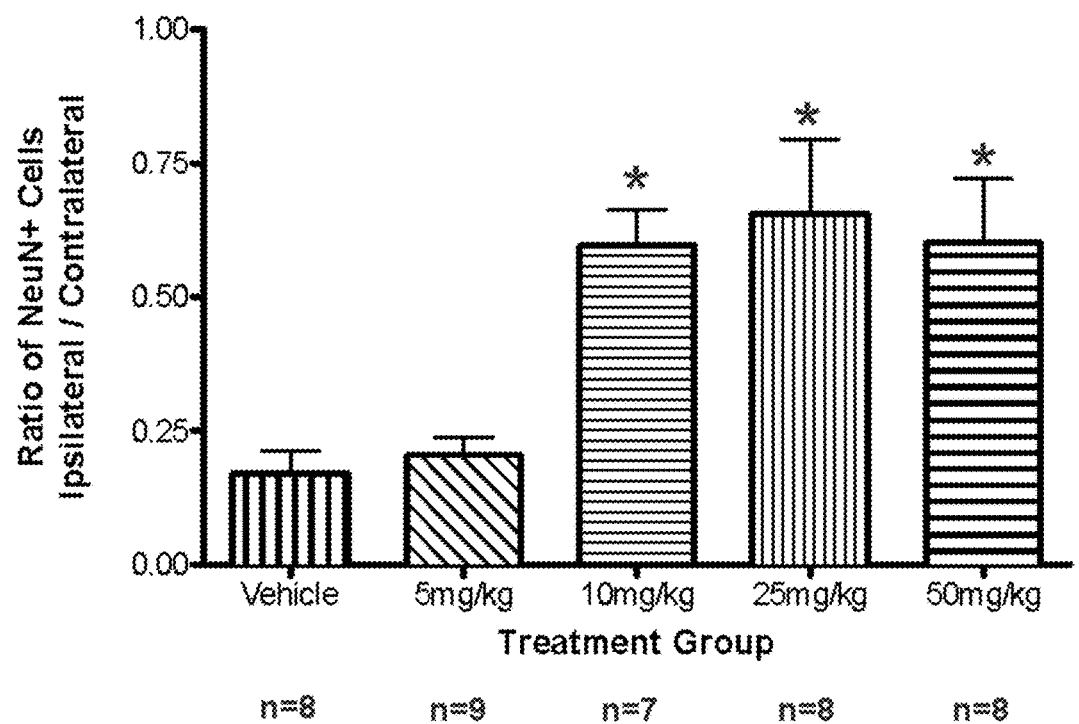
FIG. 11 illustrates a dose-dependent reduction of HI-induced striatal neuron loss produced by F4.

This study was conducted to explore optimal dosing parameters of F4 in reducing the damaging effects of HI brain injury in two vulnerable forebrain structures—dorsal hippocampus and striatum. For both structures, an oral (p.o.) dose of F4 at 25 mg/kg, given once daily for 3 days prior to HI (FIGS. 8-11), produced significant and dramatic neuroprotection. Lower doses (5-10 mg/kg, p.o.) of F4 were less neuroprotective than 25 mg/kg (p.o.) while 50 mg/kg (p.o.) of F4 was no more effective than 25 mg/kg (p.o.). In terms of dose frequency, a single oral administration of F4 (25 mg/kg) 24 hours before HI did not attenuate HI-induced injury in the striatum (FIG. 6). Oral administration of F4 (25 mg/kg/day) for 3 days produced a reduction of neuron loss in the striatum (FIG. 7) that was not further enhanced by increasing the number of doses to 7 (FIG. 8). In the case of the hippocampus, a single dose of F4 (25 mg/kg, p.o.) did not reduce tissue damage (FIG. 9). Three doses of F4 (25 mg/kg, p.o.) produced a reduction of HI-induced hippocampal atrophy but some neuronal loss was still apparent with this dosing regime (FIG. 10). Seven doses of F4 (25 mg/kg, p.o.) did, however, prevent the loss of hippocampal neurons in this structure (FIG. 11). These differences likely reflect the fact that the hippocampus is more vulnerable to HI damage than the striatum. Relative to the striatum, longer treatment with F4 (25 mg/kg/day for 7 days rather than 3 days) resulted in maximal protection of the hippocampus. These findings indicate that for F4-induced neuroprotection, 25 mg/kg (p.o.) given once a day for 7 days was the optimal dosing regime in this mouse model of HI-induced brain injury.

In reference to FIG. 8, it can be seen that there is a dose-dependent reduction in HI-induced hippocampal neuron loss produced by oral (p.o.) administration of F4. NeuN staining is shown in the hippocampus ipsilateral (A, C, E, G, I) and contralateral (B, D, F, H, J) of animals exposed to 50 min of hypoxia-ischemia (HI) that received water or increasing doses of the apple peel fraction F4. Five groups, composed of 7-9 adult male C57Bl/6 mice each, were dosed orally (p.o.) once a day for 3 days with water (10 ml/kg) or F4 (5, 10, 25 or 50 mg/kg). All animals received HI 24 hours after the last administration of water or F4. F4 produced a dose-dependent reduction of tissue atrophy and neuronal loss (NeuN immunoreactive cells) in the ipsilateral hippocampus. Administration of F4 at a dose of 5 mg/kg (p.o.) did not reduce the damaging effects of HI in the ipsilateral (C) hippocampus. Administration of the 10 mg/kg (p.o.) dose of F5 partially protected the ipsilateral hippocampus (E) against brain injury caused by HI. Administration of 25 mg/kg (p.o.) (G) or 50 mg/kg (p.o.) (I) of F4 appeared to produce a near complete protection against HI-induced hippocampal injury HI.

In reference to FIG. 9, a dose-dependent reduction of HI-induced hippocampal damage by F4 can be seen. Water (10 ml/kg) or F4 (5, 10, 25 or 50 mg/kg) was administered once a day for 3 days prior to 50 minutes of HI. The last dose occurred 24 hours before HI. F4 produced a dose dependent reduction in hippocampal tissue loss. One-way ANOVA followed by Newman-Keuls comparison test. *p<0.05 relative to vehicle and F4 (5 mg/kg, p.o.) groups.

In reference to FIG. 10, a dose-dependent reduction of HI-induced striatal neuron loss produced by F4 can be seen. NeuN staining is shown in the striatum ipsilateral (A, C, E, G, I) and contralateral (B, D, F, H, J) of animals exposed to 50 min of hypoxia-ischemia (HI) that received water or increasing doses of the apple peel fraction F4. Five groups, composed of 7-9 adult male C57Bl/6 mice each, were dosed orally (p.o.) once a day with water (10 ml/kg) or F4 (5, 10, 25 or 50 mg/kg). All animals received HI 24 hours after the last administration of water or F4. F4 produced a dose-dependent reduction of tissue atrophy and neuronal loss (NeuN immunoreactive cells) in the ipsilateral striatum. Administration of F4 at a dose of 5 mg/kg (p.o.) did not reduce the damaging effects of HI in the ipsilateral (C) striatum. Administration of the 10 mg/kg (p.o.) dose of F4 partially protected the ipsilateral striatum (E) against brain injury caused by HI. Administration of 25 mg/kg (p.o.) (G) or 50 mg/kg (p.o.) (I) of F4 appeared to produce a near complete protection against HI-induced striatal injury HI.

In reference to FIG. 11, a dose-dependent reduction of HI-induced striatal neuron loss is produced by F4. Water (10 ml/kg) or F4 (5, 10, 25 or 50 mg/kg) was administered once a day for 3 days prior to 50 minutes of HI. The last dose occurred 24 hours before HI. F4 produced a dose dependent reduction of HI-induced neuron loss in the ipsilateral striatum. One-way ANOVA followed by Newman-Keuls comparison test. *p<0.05 relative to vehicle and F4 (5 mg/kg, p.o.) groups.

Figure 12:
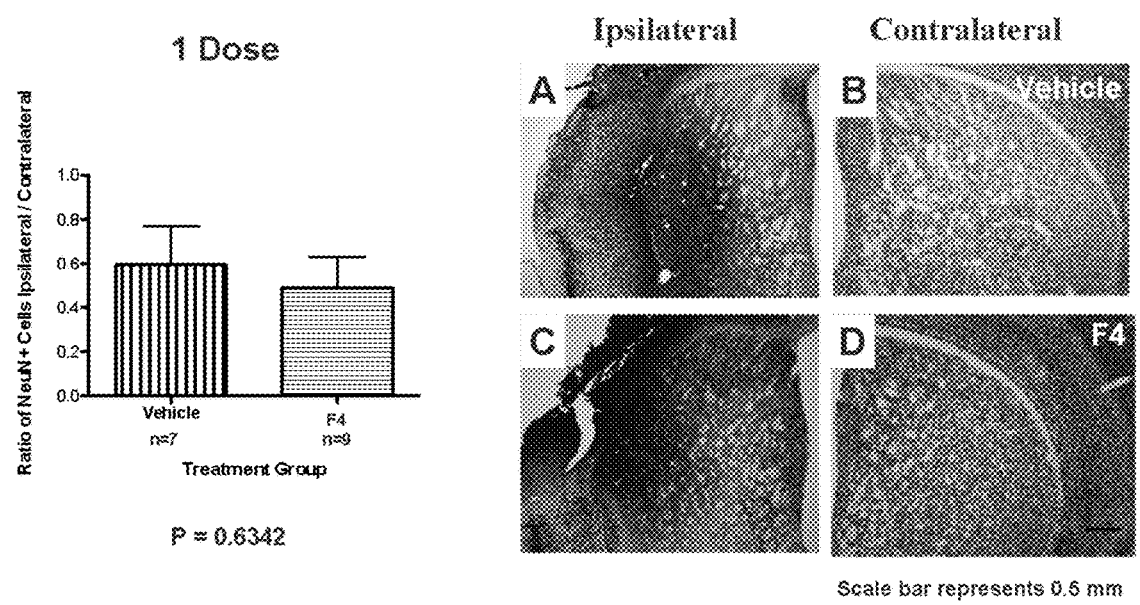
FIG. 12 illustrates a failure of one dose of F4 (25 mg/kg, p.o.) before HI to reduce striatal neuron loss.

In reference to FIG. 12. Failure of one dose of F4 (25 mg/kg, p.o.) before HI to reduce striatal neuron loss. Two groups of mice received water (10 ml/kg, p.o.) or 25 mg/kg (p.o.) of F4 and were subjected to 50 min of HI 24 hours later. Quantification of the relative number of NeuN positive neurons in the ipsilateral and contralateral striatum revealed that one dose of F4 (25 mg/kg, p.o.) failed to reduce striatal injury. Representative brain sections show NeuN immunoreactivity in the ipsilateral (A, C) and contralateral (B, D) striatum of animals that received water (A, B) or F4 (C, D) 14 days after HI.

Figure 13:
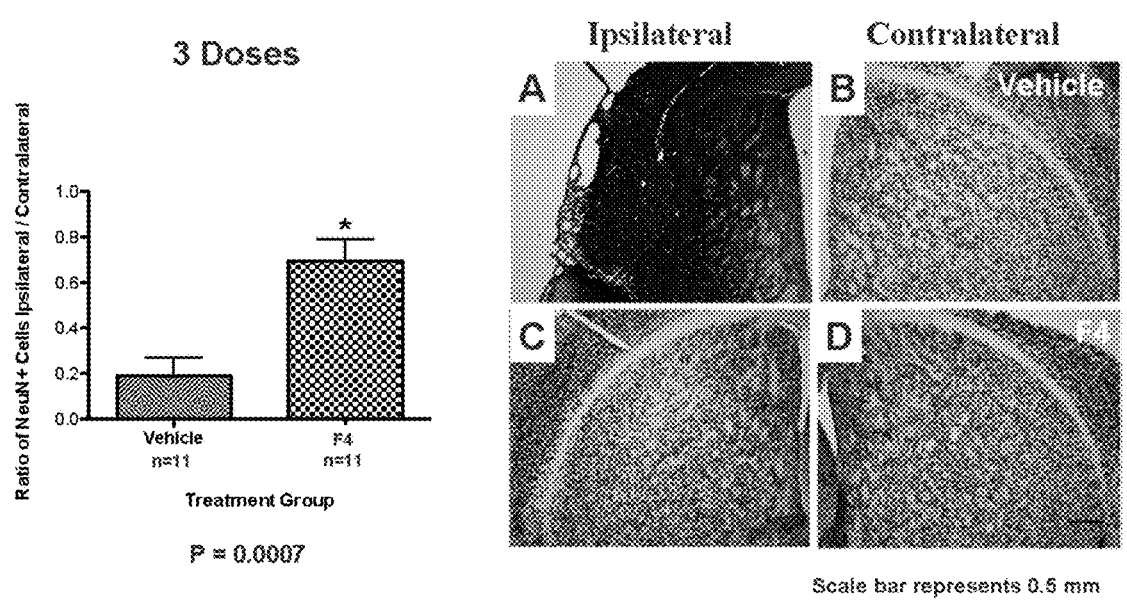
FIG. 13 illustrates a reduction of striatal neuron loss by three doses of F4 (25 mg/kg/day, p.o) before HI.

In reference to FIG. 13, it can be seen that there is a reduction of striatal neuron loss by three doses of F4 (25 mg/kg/day, p.o) before HI. Two groups of mice received water (10 ml/kg, p.o.) or 25 mg/kg (p.o.) of F5 once a day for 3 days. All animals were subjected to 50 min of HI 24 hours after the last administration of water or F4. Quantification of the relative number of NeuN positive neurons in the ipsilateral and contralateral striatum revealed that 3 doses of F4 (25 mg/kg, p.o.) reduced striatal injury. Representative brain sections show NeuN immunoreactivity in the ipsilateral (A, C) and contralateral (B, D) striatum of animals that received water (A, B) or F4 (C, D) 14 days after HI. *P<0.05, Mann-Whitney test.

Figure 14:
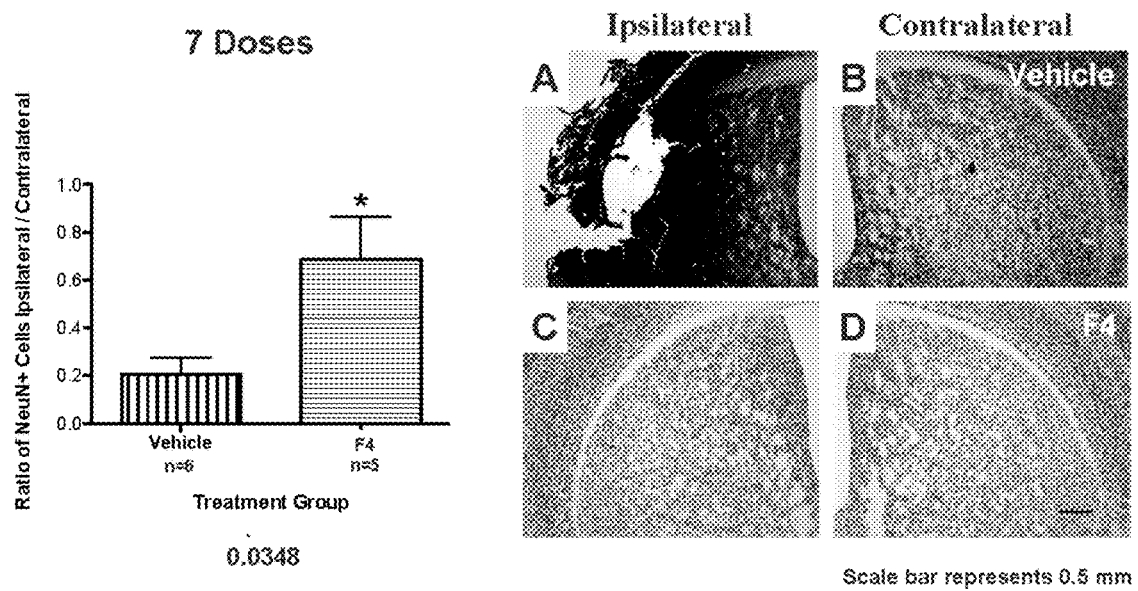
FIG. 14 illustrates a reduction of striatal neuron loss by 7 doses of F4 (25 mg/kg/day for 7 days, p.o.) before HI.

In reference to FIG. 14, there was a reduction of striatal neuron loss by seven doses of F4 (25 mg/kg/day, p.o) before HI. Two groups of mice received water (10 ml/kg, p.o.) or 25 mg/kg (p.o.) of F4 once a day for 7 days. All animals were subjected to 50 min of HI 24 hours after the last administration of water or F4. Quantification of the relative number of NeuN positive neurons in the ipsilateral and contralateral striatum revealed that 7 doses of F4 (25 mg/kg, p.o.) reduced striatal injury. Representative brain sections show NeuN immunoreactivity in the ipsilateral (A, C) and contralateral (B, D) striatum of animals that received water (A, B) or F5 (C, D) 14 days after HI. *P<0.05, Mann-Whitney test.

Figure 15:
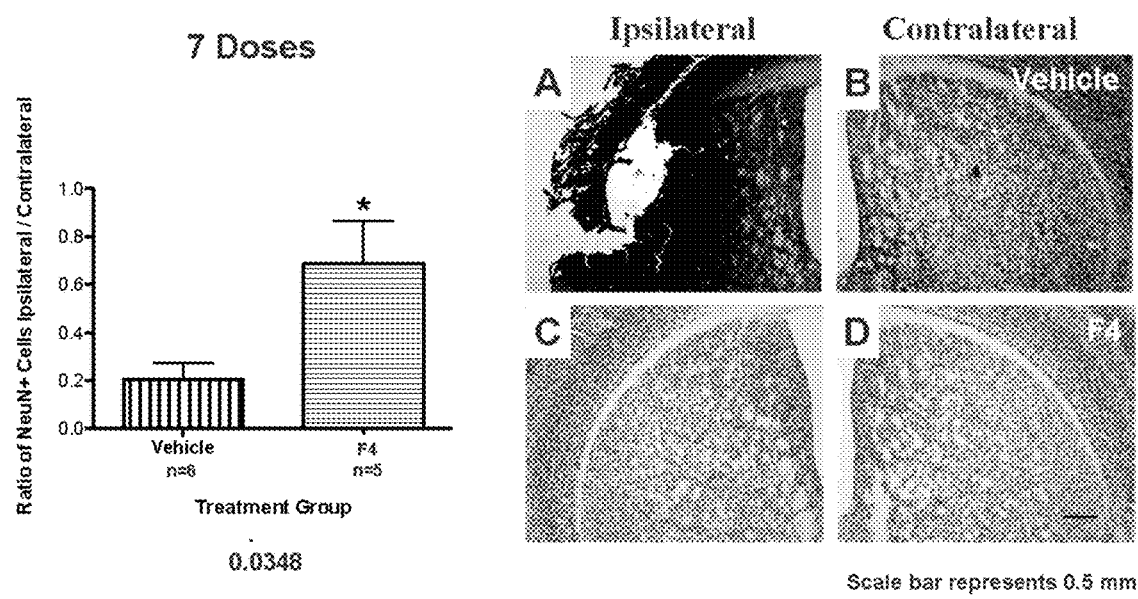
FIG. 15 illustrates that one dose of F4 (25 mg/kg, p.o.) before HI did not reduce hippocampal damage.

In reference to FIG. 15, it can be seen that one dose of F4 (25 mg/kg, p.o.) before HI did not significantly reduce hippocampal damage. Two groups of mice received water (10 ml/kg, p.o.) or 25 mg/kg (p.o.) of F5 and were subjected to 50 min of HI 24 hours later. The ability of F4 to preserve hippocampal tissue was estimated by taking a ratio of the area of this structure in the ipsilateral and contralateral hemispheres of sections stained for NeuN immunoreactivity. These measurements revealed that a single dose of F4 (25 mg/kg, p.o.) failed to reduce hippocampal injury. Representative brain sections show NeuN immunoreactivity in the ipsilateral (A, C) and contralateral (B, D) hippocampus of animals that received water (A, B) or F5 (C, D) 14 days after HI.

Figure 16:
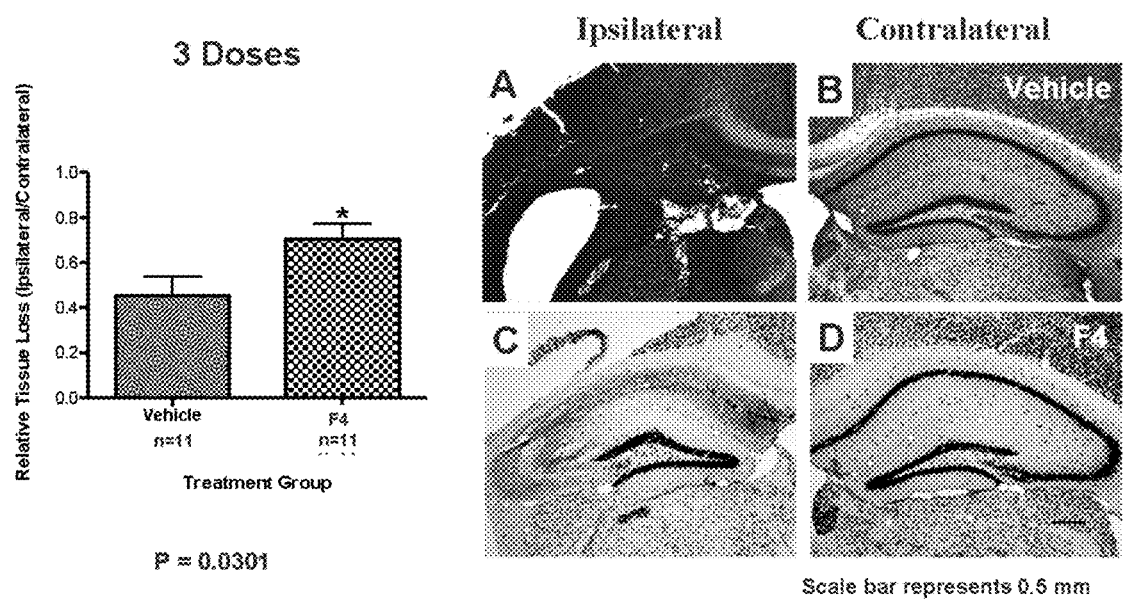
FIG. 16 illustrates that three doses of F4 (25 mg/kg, p.o.) before HI reduced hippocampal tissue loss.

In reference to FIG. 16, it can be seen that three doses of F4 (25 mg/kg, p.o.) before HI reduced hippocampal tissue loss. Two groups of mice received water (10 ml/kg, p.o.) or 25 mg/kg (p.o.) of F4 once a day for 3 days. All animals were subjected to 50 min of HI 24 hours after the last administration of water or F4. The ability of F4 to preserve hippocampal tissue was estimated by taking a ratio of the area of this structure in the ipsilateral and contralateral hemispheres of sections stained for NeuN immunoreactivity. These measurements revealed that 3 doses of F4 (25 mg/kg, p.o.) reduced hippocampal injury. Representative brain sections show NeuN immunoreactivity in the ipsilateral (A, C) and contralateral (B, D) hippocampus of animals that received water (A, B) or F5 (C, D) 14 days after HI. *P<0.05, Mann-Whitney test.

Figure 17:
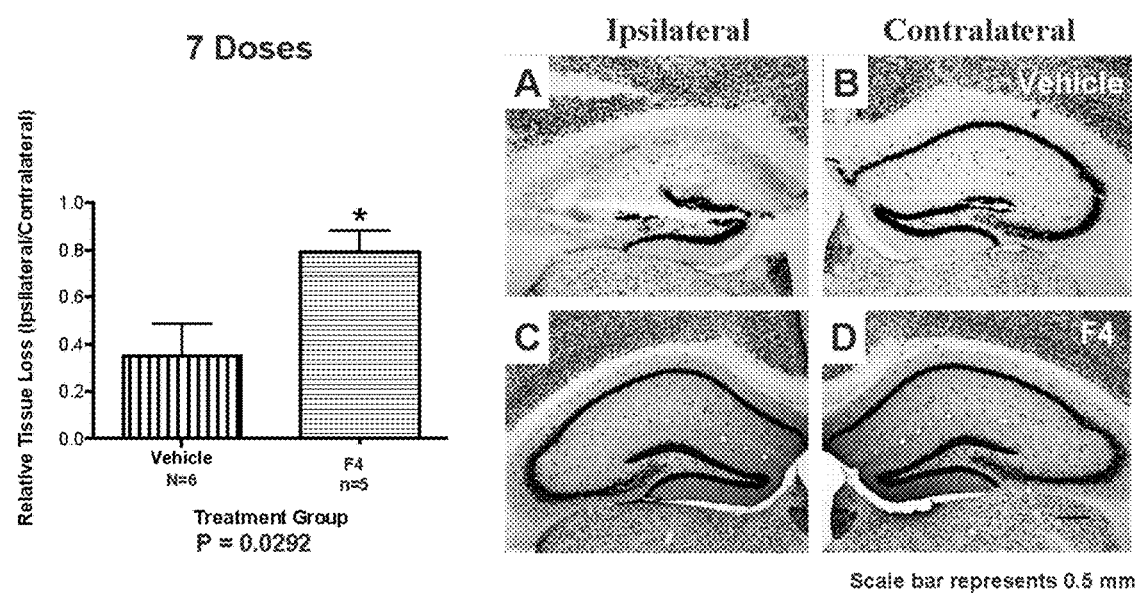
FIG. 17 illustrates that seven doses of F4 (25 mg/kg, p.o.) before HI reduced hippocampal tissue loss.

In reference to FIG. 17, it can be seen that seven doses of F4 (25 mg/kg, p.o.) before HI reduced hippocampal tissue loss. Two groups of mice received water (10 ml/kg, p.o.) or 25 mg/kg (p.o.) of F4 once a day for 7 days. All animals were subjected to 50 min of HI 24 hours after the last administration of water or F4. The ability of F4 to preserve hippocampal tissue was estimated by taking a ratio of the area of this structure in the ipsilateral and contralateral hemispheres of sections stained for NeuN immunoreactivity. These measurements revealed that 7 doses of F4 (25 mg/kg, p.o.) reduced hippocampal injury. Representative brain sections show NeuN immunoreactivity in the ipsilateral (A, C) and contralateral (B, D) hippocampus of animals that received water (A, B) or F5 (C, D) 14 days after HI. *P<0.05, Mann-Whitney test.

With regard to the studies that showed no significant protection with a single dose of F4 at 25 mg/kg, it is possible that a higher dose or a different route of administration may have resulted in a significant protective effect. The results do nonetheless show significant protection of treatment with F4 or F5 when administered at a suitable dose or dosing frequency, which can be determined by those of skill in the art.

Example 5

F4 is Effective in an Animal Model of Multiple Sclerosis

Experimental autoimmune encephalomyelitis (EAE) is a widely accepted animal model for multiple sclerosis (MS). Immunization of mice with a portion of myelin oligodendrocyte glycoprotein (MOG) encompassing amino acids 35-55 ($MOG_{35-55}$) in conjunction with Complete Freund's adjuvant results in the development of paralysis associated with neuropathology resembling MS. The present study performed to determine if oral administration of F4 after the first clinical signs of EAE were apparent (hooked tail) reduced disease progression compared to animals that received an equivalent amount of water. Disease progression was determined by assessment of the clinical signs of EAE (paralysis, walking deficits) as described below.

Methods

Female adult C57Bl/6 mice (Charles River; St. Constant, QU) 6-8 weeks old were immunized with $MOG_{35-55}$ (Sheldon Biotechnology Centre, Montreal, PQ) dissolved in 1×PBS (pH=7.4) emulsified in a 1:1 ratio with Complete Freund's adjuvant (CFA) containing 0.5 mg of *Mycobacterium tuberculosis* H37RA (Difco Laboratories; BD Diagnostics). On day 0, the $MOG_{35-55}$ emulsion was injected subcutaneously (s.c.) bilaterally at the base of the tail (300 μg/mouse). Pertussis toxin (PTX) (Sigma, St. Louis, Mo.), an immune booster, was diluted in saline and administered intraperitoneally (i.p.) (300 ng/mouse) on day 0, and again on day 2.

A health check was carried out on day 5 and mice were randomly assigned to either a treatment group (n=10) or a water group (n=10). The weights and clinical scores of each individual mouse were recorded daily over 31 days beginning on day 7. Drug (F4) or water was administered orally (25 mg/kg) immediately upon initial presentation of clinical signs and dosing continued daily for the remainder of the experiment.

The following grading scheme was used to clinically score the animals: 0, no clinical signs; 0.5, hooked tail; 1, hooked tail with splay; 1.5, flaccid tail with splay; 2, beginning of walking deficits/minor ataxia; 2.5, severe walking deficits; 3, dropped pelvis in addition to severe walking deficits; 3.5, unilateral hindlimb paralysis; 4, bilateral hindlimb paralysis; 5, moribund. Mice were supplied with mash and handfed Neutri-Cal® (Evsco Pharmaceuticals; Buena, N.J.) when they were no longer able to reach food. Lactated ringers solution (50 U/Daily) was provided when a mouse reached a score ≥2.5 or when their weight fell 10% below baseline. All clinical scores were recorded by a blinded scorer.

Results

Treatment with F4 (n=9) led to a significant reduction in clinical impairment compared to treatment with water alone (n=10; 2 way ANOVA followed by Bonferroni tests, p<0.01). One mouse was removed from the study (F4 group) due to health concerns that were unrelated to the experiment. From days 19-22, the average clinical score in the F4-EAE group peaked at ~2.5, while maximal increases in disease severity for the water-EAE group ranged from ~3.5-4. Both groups remitted; however, the F4 group recovered more rapidly and showed a trend toward complete recovery while the water group began to relapse on day 31.

The ability of F4 to reduce the severity of EAE in mice suggests that it has the potential to halt disease progression in patients with multiple sclerosis, an important facet of MS treatment.

Figure 18:
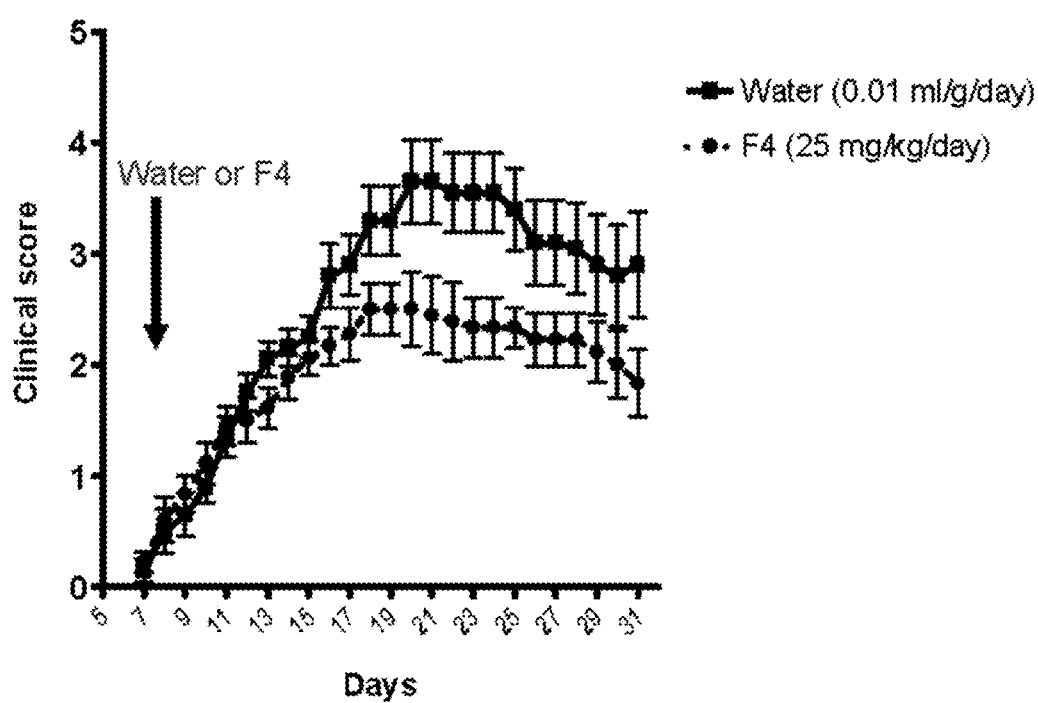
FIG. 18 illustrates that oral administration of F4 (25 mg/kg p.o) beginning 24 hours after first clinical signs of EAE reduced disease progression compared to animals that received water.

In reference to FIG. 18, it can be seen that F4 significantly ameliorates clinical severity in EAE. Female C57Bl/6 mice were immunized with $MOG_{35-55}$ (300 μg/mouse) in a 1:1 ratio with CFA on day 0 and boosted with pertussis toxin injections (300 ng/mouse) on days 0 and 2. The weights and clinical scores of each individual mouse were recorded daily over 31 days beginning on day 7. Oral administration of F4 (25 mg/kg) or vehicle (water 10 ml/kg) was administered 24 hours after the first presentation of clinical signs and dosing continued daily for the remainder of the experiment. By day 10, all mice presented with clinical signs and were being dosed with their respective treatment (downward arrow). The following grading scheme was used to clinically score the animals: 0, no clinical signs; 0.5, hooked tail; 1, hooked tail with splay; 1.5, flaccid tail with splay; 2, beginning of walking deficits and ataxia; 2.5, severe walking deficits; 3, dropped pelvis in addition to severe walking deficits; 3.5, unilateral hindlimb paralysis; 4, bilateral hindlimb paralysis; 5, moribund. Relative to EAE-water group (n=10), EAE-F4 animals (n=9) displayed less severe clinical scores and did not relapse (2 way ANOVA followed by Bonferroni tests, p<0.01). From days 19-22 the average clinical score in the F4-EAE group peaked at ~2.5, while maximal increases in disease severity for the water-EAE group ranged from ~3.5-4.

Example 6

F4 Reduces LPS-Induced TNF-α Release

Methods

Two groups, composed of 15 adult male C57BL/6 (25 g) mice each, were dosed orally with water (0.01 μg) or F4 (50 mg/kg) every 24 h for 3 days. Twenty-four hours after the last administration of water of F4, animals from each of these two groups were subject to either sham HI surgery (n=10) or 50 min of HI (n=5). Either 16 hours later (no injury) or 6 hours later (injury), whole blood was collected into microtainers containing lithium heparin (BD Biosciences, Franklin Lakes, N.J.) from all mice. LPS (lipopolysaccharide, serotype 0111:B4; Sigma-Aldrich, St. Louis, Mo.) derived from *Escherichia coli* (100 µg) was used to induce the release of TNF-α, a surrogate marker for activation of the pro-inflammatory enzyme phosphodiesterase 4 mouse whole blood according to Moore et al. (2006). Freshly prepared LPS was prepared at a concentration of 5 mg/ml in 0.1% bovine serum albumin in phosphate-buffered saline and diluted to a final concentration of 100 µg of LPS/ml of blood. The blood was incubated for 4 h at 37° C. in a humidified tissue culture incubator supplemented with 5% $CO_2$. Following this incubation, blood was centrifuged at 1400 g for 10 min at 4° C., and the plasma was collected and stored at −80° C. LPS-induced TNF-α release in whole blood was assessed using an ELISA and performed according to the manufacturer's protocol (BioSource International, Camarillo, Calif.). In brief, using a solid-phase sandwich ELISA and a streptavidin-peroxidase reaction, the intensity of the colored product is directly proportional to the amount of TNF-α in the sample. The absorbance was read at 450 nm blanked against a chromagen blank, and the amount of TNF-α in each sample was calculated using a recombinant mouse TNF-α.

Results

Figure 19:
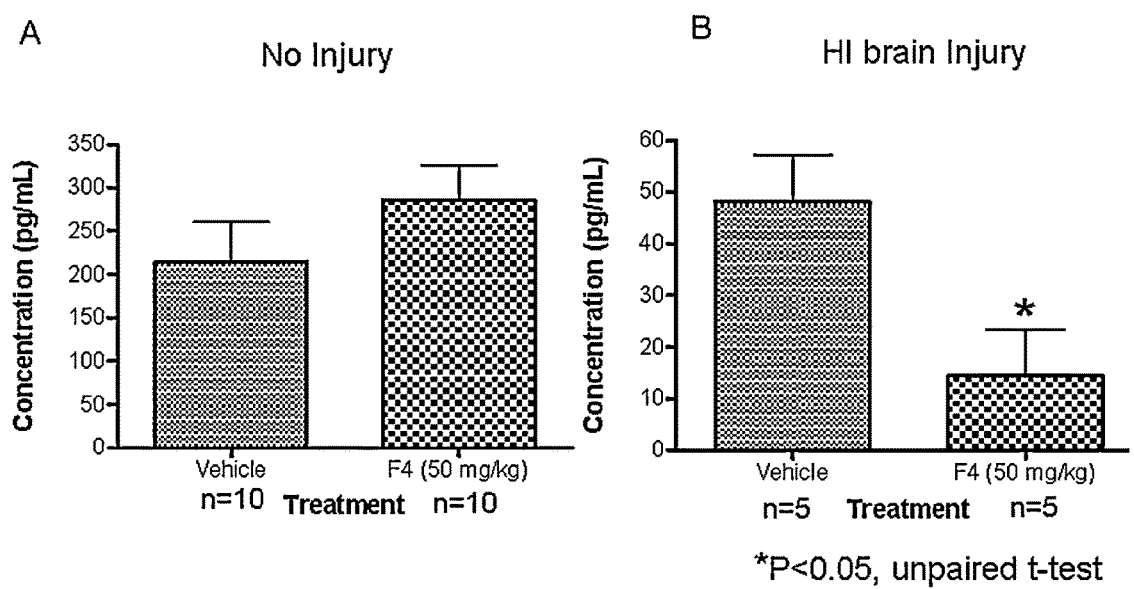
FIG. 19 illustrates that oral administration of F4 (50 m/kg) reduces production of the inflammatory cytokine tumour necrosis factor alpha (TNFα) in LPS-stimulated whole blood from mice subjected to HI. A, LPS-induced TNF-α release was the same in whole blood from sham treated animals (no brain injury) received oral administration of water or F4. B, LPS-induced TNF-α release was the greater in whole blood from HI animals (brain injury) that received oral administration of water compared to mice that received F4.

In reference to FIG. 19, A, LPS-induced TNF-α release was the same in whole blood from sham treated animals (no brain injury) who received oral administration of water or F4. B, LPS-induced TNF-α release was the greater in whole blood from HI animals (brain injury) that received oral administration of water compared to mice that received F4. These results suggests that F4 has a potent anti-inflammatory effect in the presence of brain injury but, advantageously, will not act as a general immunosuppressant in healthy individuals.

CONCLUSIONS

These results suggest that F4 reduces HI brain injury by decreasing production of the pro-inflammatory cytokine TNF-α in whole blood that would otherwise mobilize the innate immune system resulting in infiltration of damaging immune cells such as macrophages and neutrophils in the central nervous system. Flavonoids such as quercetin are known to block the phosphodiesterase 4 (Pleuso, 2006). Since LPS-induced TNF-α is inhibited in whole blood from animals treated with doses of selective phosphodiesterase 4 inhibitors block doses that prevent the clinical signs of EAE (Moore et al, 2006), our results indicate the F4 reduced neurodegeneration in the HI and EAE models by inhibiting this pro-inflammatory enzyme.

It should be noted that the results for Fractions F4 and F5 were similar in all studies where both fractions were tested.

The above-described embodiments are intended to be examples only. Alterations, modifications and variations can be effected to the particular embodiments by those of skill in the art without departing from the scope of the disclosure, which is defined solely by the claims appended hereto.

REFERENCES

Heo H J, Kim D O, Choi S J, Shin D H and Lee C Y, 2004. Apple phenolics protect in vitro oxidative stress-induced neuronal cell death. J Food Sci 69, S357-S360

Gugler R et al. 1975 Eur. J. Clin. Pharmacol. 9: 229

Huber G. M. and Rupasinghe, 2009. Phenolic Profiles and Antioxidant Properties of Apple Skin Extracts. J Food Chem, 74(9): C693-C700.

Kaur and Kapoor, 2001. Antioxidants in fruits and vegetables—millenium's health. International J Food Sci Tec 36, 703-725.

Kim et al., 2005. Phenolic Extraction from Apple Peel by Cellulases from *Thermobifidia fusca*. J Agric Food Chem, 53, 9560-9565.

Kondo et al., 2002. Antioxidative activity of apple skin or flesh extracts associated with fruit development on selected apple cultivars. Sci Horticult 96(1-4), 177.

Levine, S., 1960. Anoxic-ischemic encephalopathy in rats. Am J Pathol. 36, 1-17.

C. S. Moore, N. Earl, R. Frenette, A. Styhler, J. A. Mancini, D. W. Nicholson, A. L. O. Hebb, T. Owens, and G. S. Robertson 2006 Journal of Pharmacology and Experimental Therapeutics 319, 63-72

Pleuso M. R. Exp Biol Med 231:1287-1299, 2006

Rupasinghe, H. P. V., N. Erkan, and A. Yasmin. 2010. Antioxidant protection of eicosapentaenoic acid and fish oil oxidation by polyphenolic-enriched apple skin extract. J. Agric. Food Chem. 58:1233-1239.

Rutz, M. J. et al. 2009. Dietary administration of high doses of pterostilbene and quercetin to mice is not toxic. J. Agric. Food Chem 57(8): 3180-6.

Soundararajan et al. 2008. Quercetin 3-glucoside protects neuroblastoma (SYH-SY5Y) cells in vitro against oxidative damage by inducing sterol regulatory element-binding protein-2-mediated cholesterol biosynthesis. JBC, January 25, 283 (34), 2231-2245.

Williams R J et al. Free Radical Biology and Medicine. Volume 36, Issue 7, 1 Apr. 2004, Pages 838-849

Wolfe K L, Liu R H 2003. Apple peels as a value-added food ingredient. J Argic Food Chem, 51(6), 1676-83.

Wolfe K, Wu X, Liu R H 2003. Antioxidant activity of apple peels. J Agric Food Chem, 51, 609-614.

All referenced documents are incorporated herein in their entirety

The invention claimed is:

1. A pharmaceutical composition for use in treating a disease or condition associated with oxidative stress or inflammation, the composition comprising:
   an extract or fraction thereof derived from apple skin, the extract or fraction thereof comprising from about 60.0% to about 95.0% of a flavonol component; and
   an excipient or an active ingredient,
   wherein the flavonol component comprises: quercetin, quercetin-3-O-paltoside, quercetin-3-O-rutinoside, quercetin-3-O-galactoside, quercetin-3-O-glucoside, quercetin-3-O-rhamnoside, or a combination thereof,
   wherein the percentage of the flavanol component is based on the total weight of phenolic content in the extract or fraction thereof.

2. The pharmaceutical composition of claim 1, wherein the extract or fraction thereof comprises:
   from about 10.0% to about 60.0%, from about 15.0% to about 50.0%, from about 20.0% to about 50.0%, from about 20.0% to about 35.0%, from about 20.0% to about 30.0%, or from about 20.0% to about 25.0% quercetin-3-O-galactoside;
   from about 10.0% to about 60.0%, from about 15.0% to about 50.0%, from about 20.0% to about 50.0%, from about 20.0% to about 40.0%, from about 20.0% to about 35.0%, from about 20.0% to about 30.0%, from about 20.0% to about 25.0%, or from about 30.0% to about 35.0% quercetin-3-O-rhamnoside;

from about 1.0% to about 20.0%, from about 5.0% to about 15.0%, from about 7.0% to about 13.0%, from about 5.0% to about 10.0%, or from about 10.0% to about 15.0% quercetin-3-O-rutinoside; and from about 1.0% to about 20.0%, from about 5.0% to about 15.0%, from about 7.0% to about 13.0%, from about 10.0% to about 15.0%, or from about 10.0% to about 15.0% quercetin-3-O-glucoside.

3. The pharmaceutical composition of claim 2, which comprises:

from about 20.0% to about 30.0% quercetin-3-O-galactoside;

from about 20.0% to about 30.0% quercetin-3-O-rhamnoside;

from about 10.0% to about 15.0%, quercetin-3-O-rutinoside;

from about 10.0% to about 15.0%, quercetin-3-O-glucoside.

4. The pharmaceutical composition of claim 2, which comprises:

from about 20.0% to about 35.0% quercetin-3-O-galactoside;

from about 20.0% to about 35.0% quercetin-3-O-rhamnoside;

from about 5.0% to about 15.0% quercetin-3-O-rutinoside;

from about 5.0% to about 15.0% quercetin-3-O-glucoside.

5. The pharmaceutical composition of claim 1, wherein the extract is obtainable by an aqueous extraction process having the following steps:

obtaining a sample of apple skins;

treating the skins to inhibit degradation of phenolic compounds;

extracting the skins one or more times with a food-grade solvent;

removing solids to obtain the extract.

6. The pharmaceutical composition of claim 5, wherein the food-grade solvent is ethanol.

7. The pharmaceutical composition of claim 5, wherein the extract is purified and the pharmaceutical composition comprises the purified extract.

8. The pharmaceutical composition of claim 7, wherein the purified extract is obtainable by fractionating the extract using a suitable eluent, and selecting a fraction comprising between about 60.0% to about 95.0% of a flavonol component, wherein the percentage of the flavanol component is based the total weight of phenolic content in the extract or fraction thereof.

9. The pharmaceutical composition of claim 8, wherein the fraction is eluted in about 40% to about 60% ethanol.

10. The pharmaceutical composition of claim 1, wherein the excipient is a pharmaceutically acceptable carrier, diluent, or additive.

11. The pharmaceutical composition of claim 1, wherein the disease or condition associated with oxidative stress and/or inflammation is: aging, an autoimmune disorder, a neurodegenerative disorder, a metabolic disorder, or a vascular disorder.

12. The pharmaceutical composition of claim 11, wherein the vascular disorder is stroke.

13. The pharmaceutical composition of claim 11, wherein the neurodegenerative disease is multiple sclerosis, vascular dementia, Parkinson's disease, or Alzheimer's disease.

14. The pharmaceutical composition of claim 1, which is formulated for enteral administration, topical administration, parenteral administration, intrapulmonary administration, or nasal administration.

15. A method of treating a disease or condition associated with oxidative stress and/or inflammation, the method comprising administering to a subject an effective amount of an extract or fraction thereof derived from apple skin, wherein the extract or fraction thereof comprises from about 60.0% to about 95.0% of a flavonol component;

wherein the flavonol component comprises: quercetin, quercetin-3-O-paltoside, quercetin-3-O-rutinoside, quercetin-3-O-galactoside, quercetin-3-O-glucoside, quercetin-3-O-rhamnoside, or a combination thereof; and wherein the percentage of the flavanol component is based on the total weight of phenolic content in the extract or fraction thereof.

16. The method of claim 15, wherein the disease or condition associated with oxidative stress and/or inflammation is: aging, an autoimmune disorder, a neurodegenerative disorder, a metabolic disorder, or a vascular disorder.

17. The method of claim 16, wherein the vascular disorder is stroke.

18. The method of claim 16, wherein the neurodegenerative disease is multiple sclerosis, vascular dementia, Parkinson's disease, or Alzheimer's disease.

19. The method of claim 15, wherein the extract or fraction thereof is administered in the form of: a concentrate, a liquid, a powder, an emulsion, a suspension, a paste, a gel, a film, a gum, a drop, a tablet, a capsule, a microcapsule, or a food additive.

20. A dietary supplement, natural health product, functional food, or beverage for reducing damage due to oxidative stress, the dietary supplement, natural health product, functional food, or beverage comprising a food additive or food ingredient, and an extract or fraction thereof derived from apple skin, wherein the extract or fraction thereof comprises from about 60.0% to about 95.0% of a flavonol component, wherein the flavonol component comprises: quercetin, quercetin-3-O-paltoside, quercetin-3-O-rutinoside, quercetin-3-O-galactoside, quercetin-3-O-glucoside, quercetin-3-O-rhamnoside, or a combination thereof; and wherein the percentage of the flavanol component is based on the total weight of phenolic content in the extract or fraction thereof.

21. A pharmaceutical composition for use in treating, reducing the occurrence of, or ameliorating the symptoms of: stroke, ischemia, multiple sclerosis or inflammation, the composition comprising:

an extract or fraction thereof derived from apple skin, the extract or fraction thereof comprising from about 60.0% to about 95.0% of a flavonol component; and an excipient or an active ingredient, wherein the flavonol component comprises: quercetin, quercetin-3-O-paltoside, quercetin-3-O-rutinoside, quercetin-3-O-galactoside, quercetin-3-O-glucoside, quercetin-3-O-rhamnoside, or a combination thereof, wherein the percentage of the flavanol component is based on the total weight of phenolic content in the extract or fraction thereof.

22. The pharmaceutical composition of claim 21, wherein the extract or fraction thereof comprises:

from about 10.0% to about 60.0%, from about 15.0% to about 50.0%, from about 20.0% to about 50.0%, from about 20.0% to about 35.0%, from about 20.0% to about 30.0%, or from about 20.0% to about 25.0% quercetin-3-O-galactoside;

from about 10.0% to about 60.0%, from about 15.0% to about 50.0%, from about 20.0% to about 50.0%, from about 20.0% to about 40.0%, from about 20.0% to about 35.0%, from about 20.0% to about 30.0%, from about 20.0% to about 25.0%, or from about 30.0% to about 35.0% quercetin-3-O-rhamnoside;

from about 1.0% to about 20.0%, from about 5.0% to about 15.0%, from about 7.0% to about 13.0%, from about 5.0% to about 10.0%, or from about 10.0% to about 15.0% quercetin-3-O-rutinoside; and from about 1.0% to about 20.0%, from about 5.0% to about 15.0%, from about 7.0% to about 13.0%, from about 10.0% to about 15.0%, or from about 10.0% to about 15.0% quercetin-3-O-glucoside.

23. The pharmaceutical composition of claim 22, which comprises:
   from about 20.0% to about 30.0% quercetin-3-O-galactoside;
   from about 20.0% to about 30.0% quercetin-3-O-rhamnoside;
   from about 10.0% to about 15.0%, quercetin-3-O-rutinoside;
   from about 10.0% to about 15.0%, quercetin-3-O-glucoside.

24. The pharmaceutical composition of claim 22, which comprises:
   from about 20.0% to about 35.0% quercetin-3-O-galactoside;
   from about 20.0% to about 35.0% quercetin-3-O-rhamnoside;
   from about 5.0% to about 15.0% quercetin-3-O-rutinoside;
   from about 5.0% to about 15.0% quercetin-3-O-glucoside.

25. The pharmaceutical composition of claim 21, wherein the extract is obtainable by an aqueous extraction process having the following steps:
   obtaining a sample of apple skins;
   treating the skins to inhibit degradation of phenolic compounds;
   extracting the skins one or more times with a food-grade solvent;
   removing solids to obtain the extract.

26. The pharmaceutical composition of claim 25, wherein the food-grade solvent is ethanol.

27. The pharmaceutical composition of claim 25, wherein the extract is purified and the pharmaceutical composition comprises the purified extract.

28. The pharmaceutical composition of claim 27, wherein the purified extract is obtainable by fractionating the extract using a suitable eluent, and selecting a fraction comprising between about 60.0% to about 95.0% of a flavonol component, wherein the percentage of the flavanol component is based the total weight of phenolic content in the extract or fraction thereof.

29. The pharmaceutical composition of claim 28, wherein the fraction is eluted in about 40% to about 60% ethanol.

30. The pharmaceutical composition of claim 21, wherein the excipient is a pharmaceutically acceptable carrier, diluent, or additive.

31. The pharmaceutical composition of claim 21, which is formulated for enteral administration, topical administration, parenteral administration, intrapulmonary administration, or nasal administration.

32. A method of treating, reducing the occurrence of, or ameliorating the symptoms of: stroke, ischemia, multiple sclerosis or inflammation, the method comprising administering to a subject an effective amount of an extract or fraction thereof derived from apple skin,
   wherein the extract or fraction thereof comprises from about 60.0% to about 95.0% of a flavonol component;
   wherein the flavonol component comprises: quercetin, quercetin-3-O-paltoside, quercetin-3-O-rutinoside, quercetin-3-O-galactoside, quercetin-3-O-glucoside, quercetin-3-O-rhamnoside, or a combination thereof; and
   wherein the percentage of the flavanol component is based on the total weight of phenolic content in the extract or fraction thereof.

33. The method of claim 32, wherein the extract or fraction thereof is administered in the form of: a concentrate, a liquid, a powder, an emulsion, a suspension, a paste, a gel, a film, a gum, a drop, a tablet, a capsule, a microcapsule, or a food additive.

34. A dietary supplement, natural health product, functional food, or beverage for treating, reducing the occurrence of, or ameliorating the symptoms of: stroke, ischemia, multiple sclerosis or inflammation, the dietary supplement, natural health product, functional food, or beverage comprising a food additive or food ingredient, and an extract or fraction thereof derived from apple skin,
   wherein the extract or fraction thereof comprises from about 60.0% to about 95.0% of a flavonol component,
   wherein the flavonol component comprises: quercetin, quercetin-3-O-paltoside, quercetin-3-O-rutinoside, quercetin-3-O-galactoside, quercetin-3-O-glucoside, quercetin-3-O-rhamnoside, or a combination thereof; and
   wherein the percentage of the flavanol component is based on the total weight of phenolic content in the extract or fraction thereof.

* * * * *